(12) United States Patent
Stulen et al.

(10) Patent No.: US 11,678,903 B2
(45) Date of Patent: Jun. 20, 2023

(54) ULTRASONIC SURGICAL INSTRUMENT WITH ARTICULATING END EFFECTOR HAVING A CURVED BLADE

(71) Applicant: Cilag GmbH International, Zug (CH)

(72) Inventors: Foster B. Stulen, Mason, OH (US); William A. Olson, Lebanon, OH (US); William B. Weisenburgh, II, Maineville, OH (US)

(73) Assignee: Cilag GmbH International, Zug (CH)

( * ) Notice: Subject to any disclaimer, the term of this patent is extended or adjusted under 35 U.S.C. 154(b) by 407 days.

(21) Appl. No.: 16/791,124

(22) Filed: Feb. 14, 2020

(65) Prior Publication Data

US 2020/0237399 A1 Jul. 30, 2020

Related U.S. Application Data

(63) Continuation of application No. 14/688,542, filed on Apr. 16, 2015, now abandoned.

(51) Int. Cl.
| | | |
|---|---|---|
| *A61B 17/32* | (2006.01) | |
| *A61B 17/00* | (2006.01) | |
| *A61B 17/29* | (2006.01) | |

(52) U.S. Cl.
CPC ........... *A61B 17/320092* (2013.01); *A61B 2017/00314* (2013.01); *A61B 2017/00318* (2013.01);
(Continued)

(58) Field of Classification Search
CPC ............................. A61B 17/320092
See application file for complete search history.

(56) References Cited

U.S. PATENT DOCUMENTS

| | | |
|---|---|---|
| 5,322,055 A | 6/1994 | Davison et al. |
| 5,766,196 A | 6/1998 | Griffiths |

(Continued)

FOREIGN PATENT DOCUMENTS

| | | |
|---|---|---|
| CN | 101772328 A | 7/2010 |
| CN | 203354581 U | 12/2013 |

OTHER PUBLICATIONS

Chinese Office Action and Search Report dated Dec. 4, 2019 for Application No. 201680021983.4, 19 pages.
(Continued)

*Primary Examiner* — Nathaniel C Chukwurah
(74) *Attorney, Agent, or Firm* — Frost Brown Todd LLP

(57) ABSTRACT

An apparatus comprises a body assembly and a shaft extending distally therefrom. The shaft defines a longitudinal axis. The apparatus further comprises an acoustic waveguide and an articulation section coupled with the shaft. A portion of the articulation section encompasses a flexible portion of the waveguide. The articulation section further comprises first member and a second member that is longitudinally translatable relative to the first member. The apparatus further comprises an end effector including an ultrasonic blade in acoustic communication with the waveguide. A distal portion the ultrasonic blade is disposed in a first direction away from the longitudinal axis at a bend angle. The end effector also includes a clamp arm that is coupled with the first member and the second member, and an articulation drive assembly operable to drive articulation of the articulation section to thereby deflect the end effector from the longitudinal axis in the first direction.

20 Claims, 35 Drawing Sheets

(52) U.S. Cl.
CPC ............ *A61B 2017/00327* (2013.01); *A61B 2017/2908* (2013.01); *A61B 2017/320069* (2017.08); *A61B 2017/320071* (2017.08); *A61B 2017/320075* (2017.08); *A61B 2017/320089* (2017.08); *A61B 2017/320093* (2017.08); *A61B 2017/320094* (2017.08); *A61B 2017/320095* (2017.08)

(56) References Cited

U.S. PATENT DOCUMENTS

| | | | |
|---|---|---|---|
| 5,873,873 | A | 2/1999 | Smith et al. |
| 5,897,523 | A | 4/1999 | Wright et al. |
| 5,980,510 | A | 11/1999 | Tsonton et al. |
| 5,989,264 | A | 11/1999 | Wright |
| 6,063,098 | A | 5/2000 | Houser et al. |
| 6,090,120 | A | 7/2000 | Wright et al. |
| 6,325,811 | B1 | 12/2001 | Messerly |
| 6,454,782 | B1 | 9/2002 | Schwemberger |
| 6,589,200 | B1 | 7/2003 | Schwemberger et al. |
| 6,752,815 | B2 * | 6/2004 | Beaupre ................ G10K 11/24 606/169 |
| 6,773,444 | B2 | 8/2004 | Messerly |
| 6,783,524 | B2 | 8/2004 | Anderson et al. |
| 7,135,030 | B2 | 11/2006 | Schwemberger et al. |
| 7,621,930 | B2 | 11/2009 | Houser |
| 8,461,744 | B2 | 6/2013 | Wiener et al. |
| 8,591,536 | B2 | 11/2013 | Robertson |
| 8,623,027 | B2 | 1/2014 | Price et al. |
| 8,986,302 | B2 | 3/2015 | Aldridge et al. |
| 9,023,071 | B2 | 5/2015 | Miller et al. |
| 9,095,367 | B2 | 8/2015 | Olson et al. |
| 9,220,559 | B2 | 12/2015 | Worrell et al. |
| 9,364,230 | B2 | 6/2016 | Shelton et al. |
| 9,393,037 | B2 * | 7/2016 | Olson ............ A61B 17/320068 |
| 9,408,622 | B2 | 8/2016 | Stulen et al. |
| 10,172,636 | B2 * | 1/2019 | Stulen ............ A61B 17/320068 |
| 2006/0079874 | A1 | 4/2006 | Faller et al. |
| 2006/0079879 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2012/0078247 | A1 | 3/2012 | Worrell et al. |
| 2012/0078248 | A1 * | 3/2012 | Worrell .............. A61B 18/1447 606/45 |
| 2012/0112687 | A1 | 5/2012 | Houser et al. |
| 2012/0116265 | A1 | 5/2012 | Houser et al. |
| 2013/0289592 | A1 | 10/2013 | Stulen et al. |
| 2014/0005701 | A1 | 1/2014 | Olson et al. |
| 2014/0005705 | A1 | 1/2014 | Weir et al. |
| 2014/0276966 | A1 | 9/2014 | Ranucci et al. |
| 2015/0080924 | A1 * | 3/2015 | Stulen ............ A61B 17/320092 606/169 |
| 2016/0302819 | A1 | 10/2016 | Stulen et al. |

OTHER PUBLICATIONS

Chinese Office Action dated Jun. 10, 2020 for Application No. 201680021983.4, 20 pages.
European Communication dated Jun. 25, 2020 for Application No. 16718182.5, 6 pages.
International Search Report and Written Opinion dated Oct. 20, 2016 for International Application No. PCT/US2016/027686, 13 pages.
Japanese Notification of Reasons for Refusal dated Mar. 6, 2020 for Application No. 2017-553980, 5 pages.
Japanese Decision of Refusal dated Oct. 14, 2020 for Application No. 2017-553980, 2 pages.
U.S. Appl. No. 61/410,603, entitled "Energy-Based Surgical Instruments," filed Nov. 5, 2010.
U.S. Appl. No. 14/258,179, entitled "Ultrasonic Surgical Device with Articulating End Effector," filed Apr. 22, 2014.
European Search Report and Written Opinion dated May 3, 2022 for Application No. EP 21217366.0, 12 pgs.

* cited by examiner

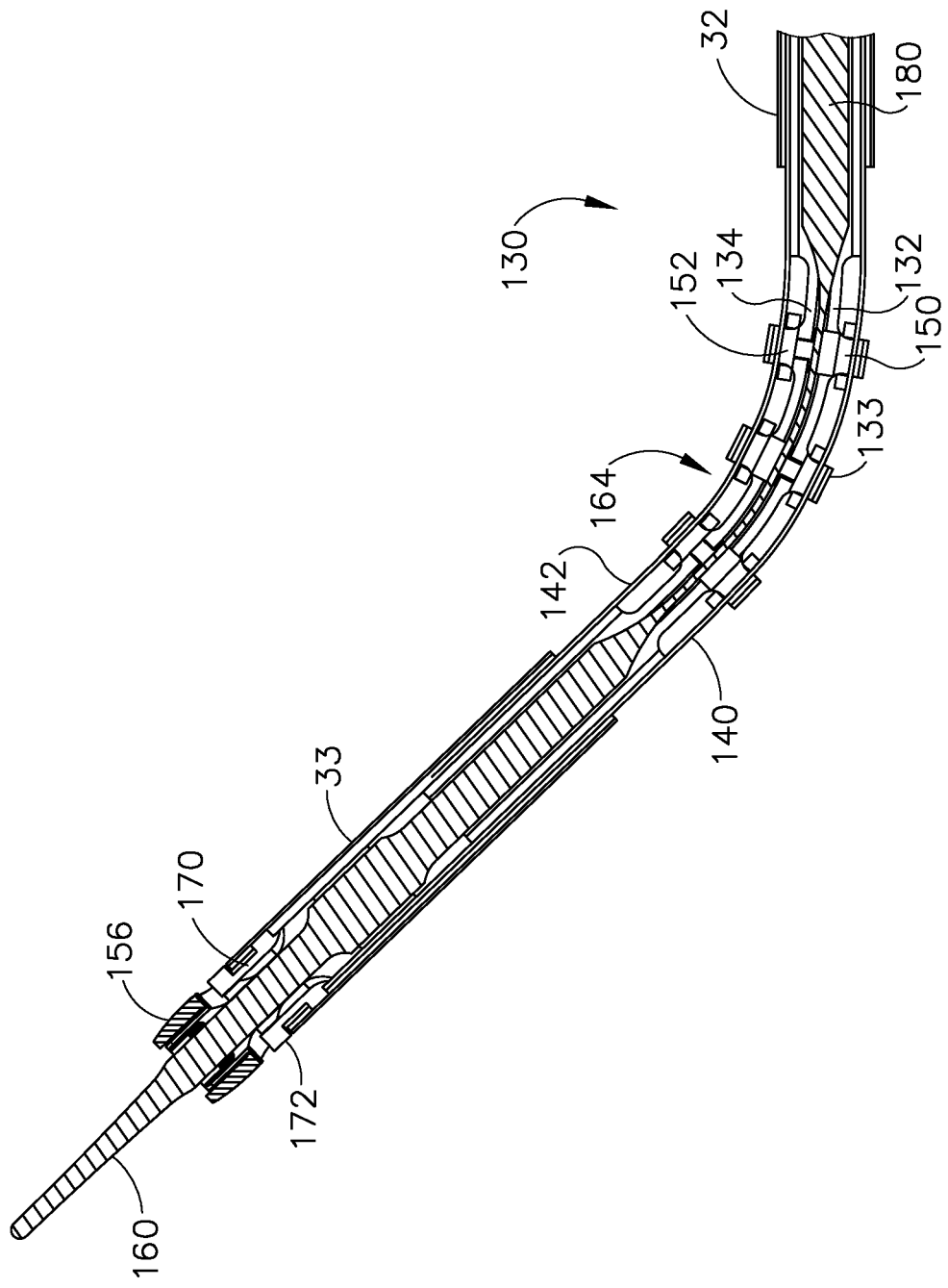

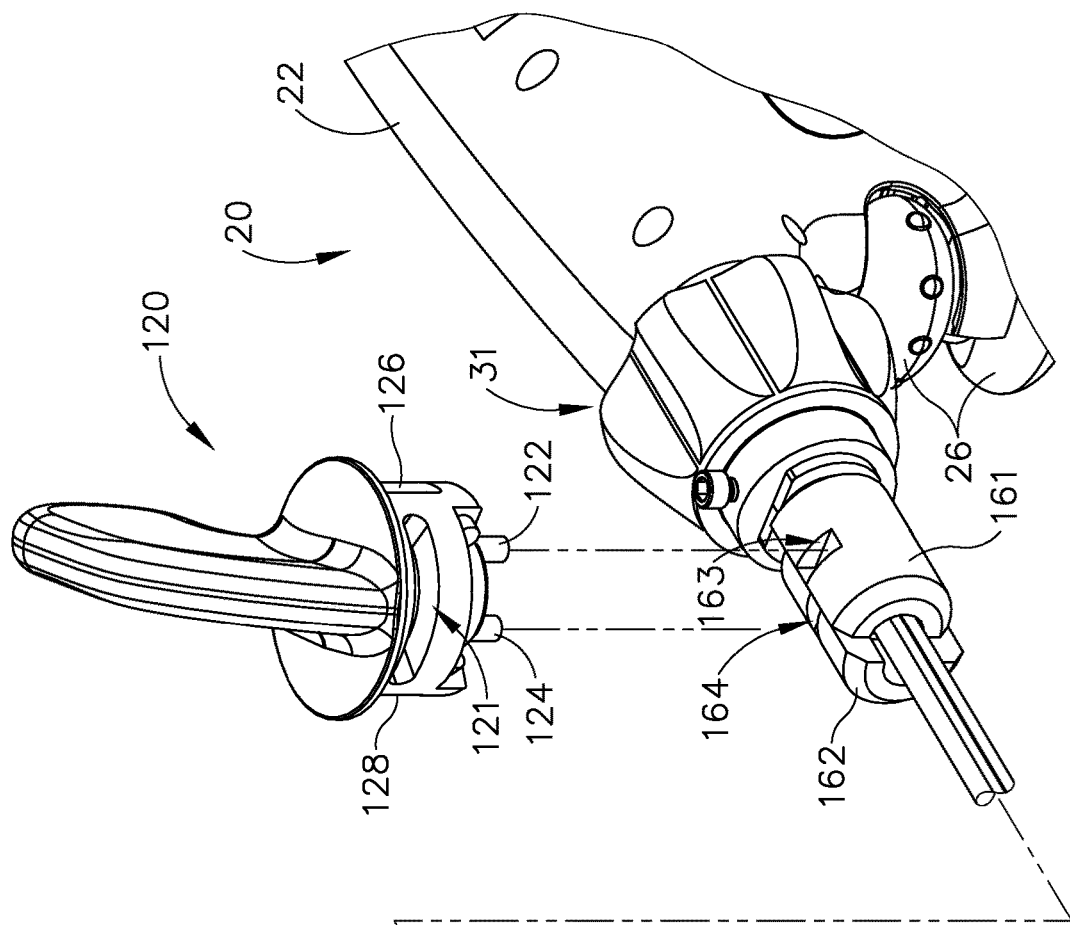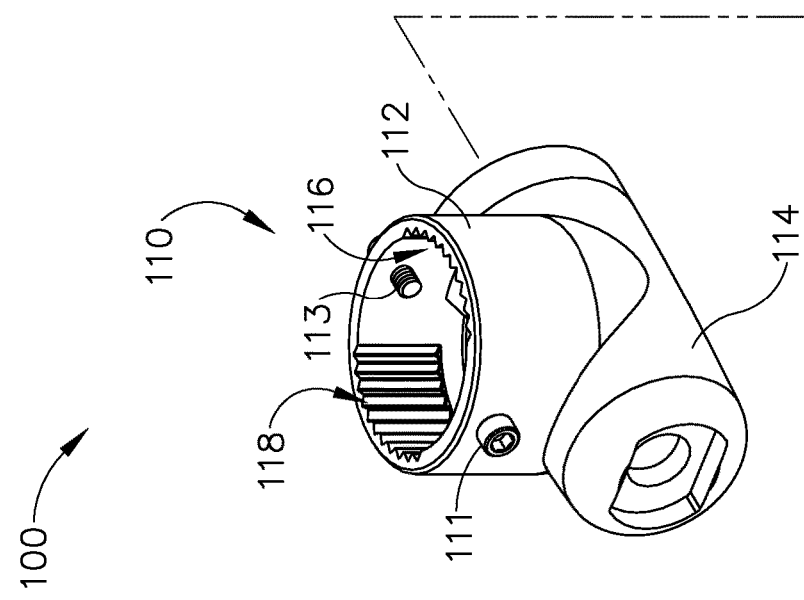
Fig. 9

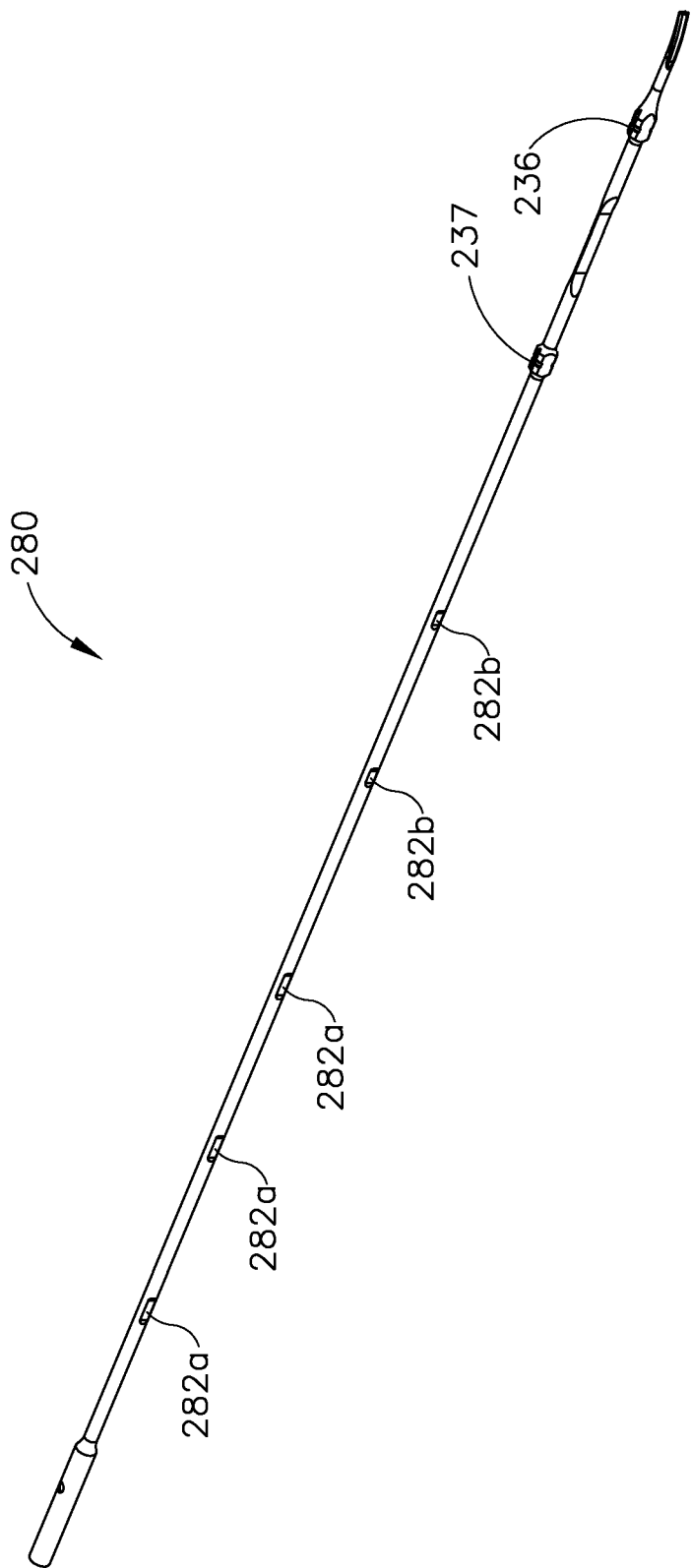

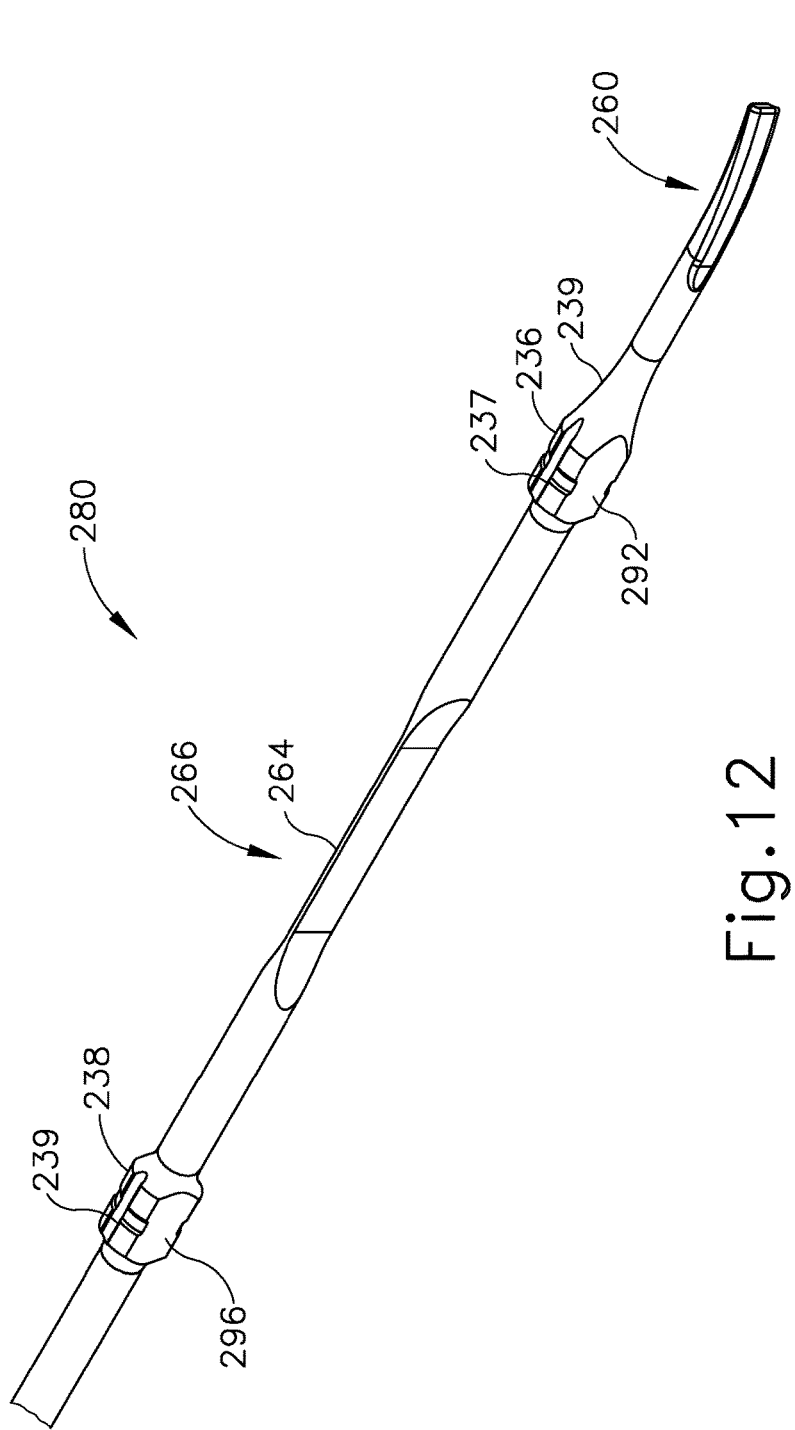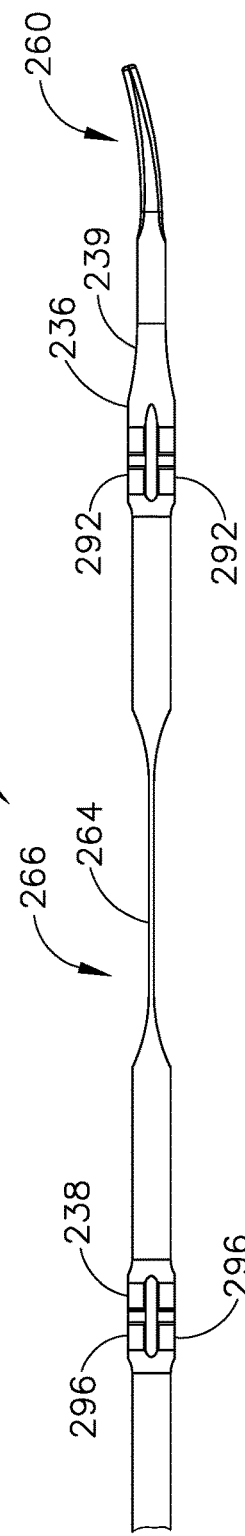

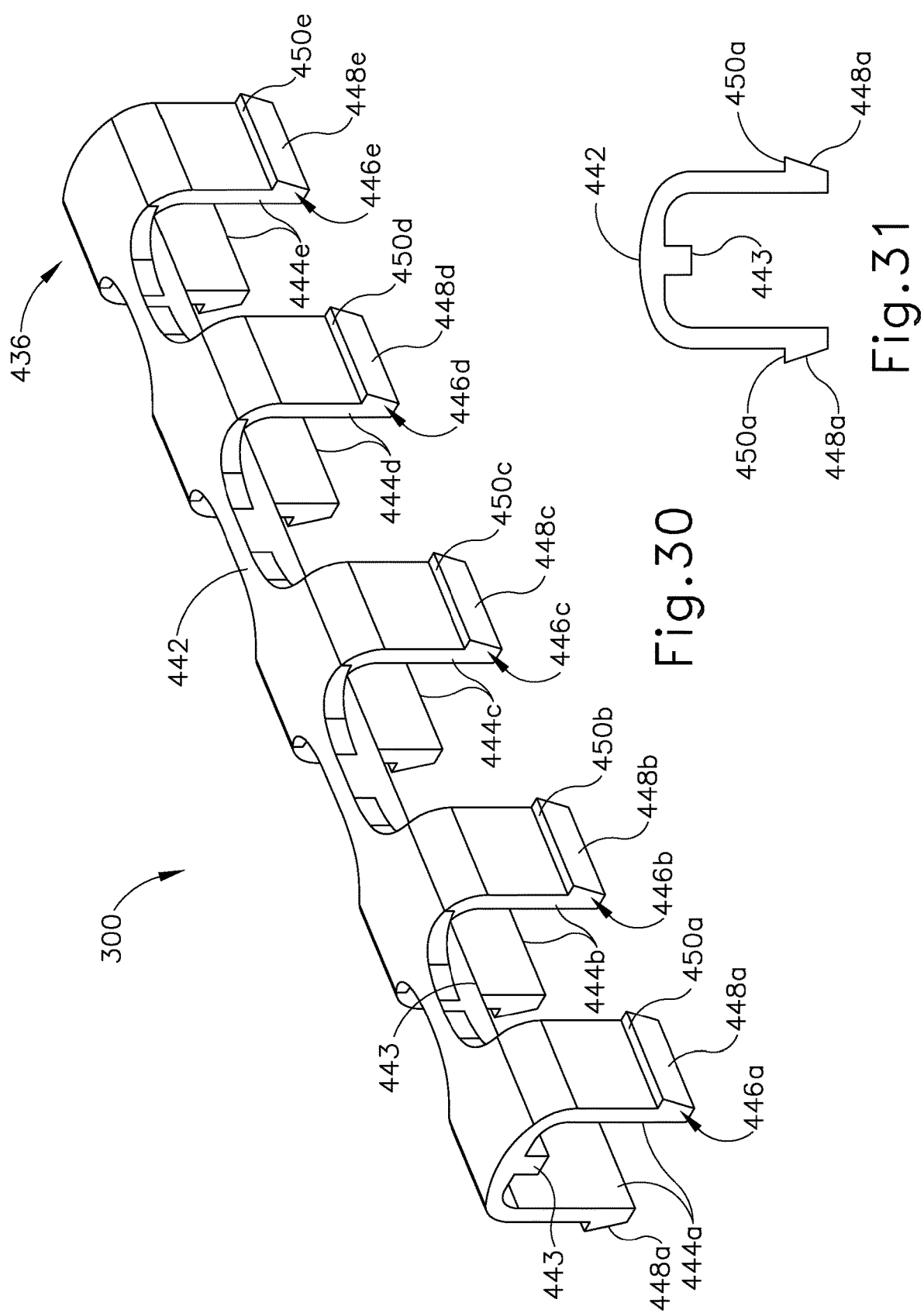

ULTRASONIC SURGICAL INSTRUMENT WITH ARTICULATING END EFFECTOR HAVING A CURVED BLADE

This application is a continuation of U.S. patent application Ser. No. 14/688,542, entitled "Ultrasonic Surgical Instrument with Articulating End Effector having a Curved Blade," filed Apr. 16, 2015, now abandoned.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, issued Nov. 9, 1999, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014 the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, isused as U.S. Pat. No. 8,986,302 on Mar. 24, 2015, the disclosure of which is incorporated by reference herein; U.S. Pub. No. 2015/0080924, entitled "Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. patent application Ser. No. 14/258,179, converted to provisional application 62/176,880, entitled Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6B depicts a cross-sectional top view of the shaft assembly and end effector of FIG. 2 in an articulated configuration;

FIG. 9 depicts a partially exploded perspective view of an articulation control assembly of the instrument of FIG. 1;

FIG. 11 depicts a perspective view of an exemplary alternative waveguide, including a curved blade;

FIG. 12 depicts a perspective view of a distal end of the waveguide of FIG. 11;

FIG. 13 depicts a top view of the distal end of the waveguide of FIG. 11, showing a bend angle of a blade of the waveguide;

FIG. 30 depicts a perspective view of a collar of the articulation section of FIG. 14;

FIG. 31 depicts a front elevational view of the collar of FIG. 30;

Figure 1:
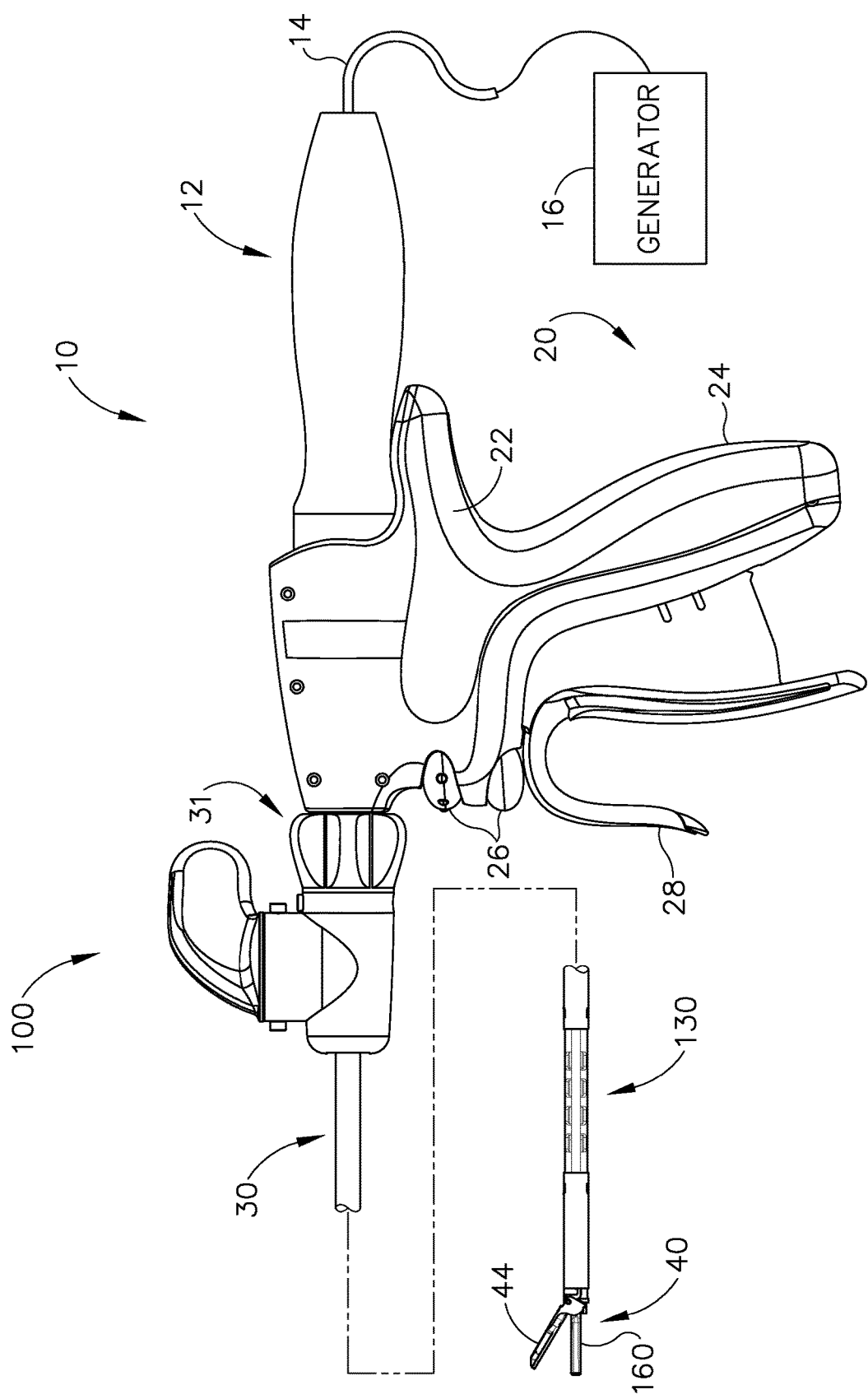
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. EXEMPLARY ULTRASONIC SURGICAL INSTRUMENT

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
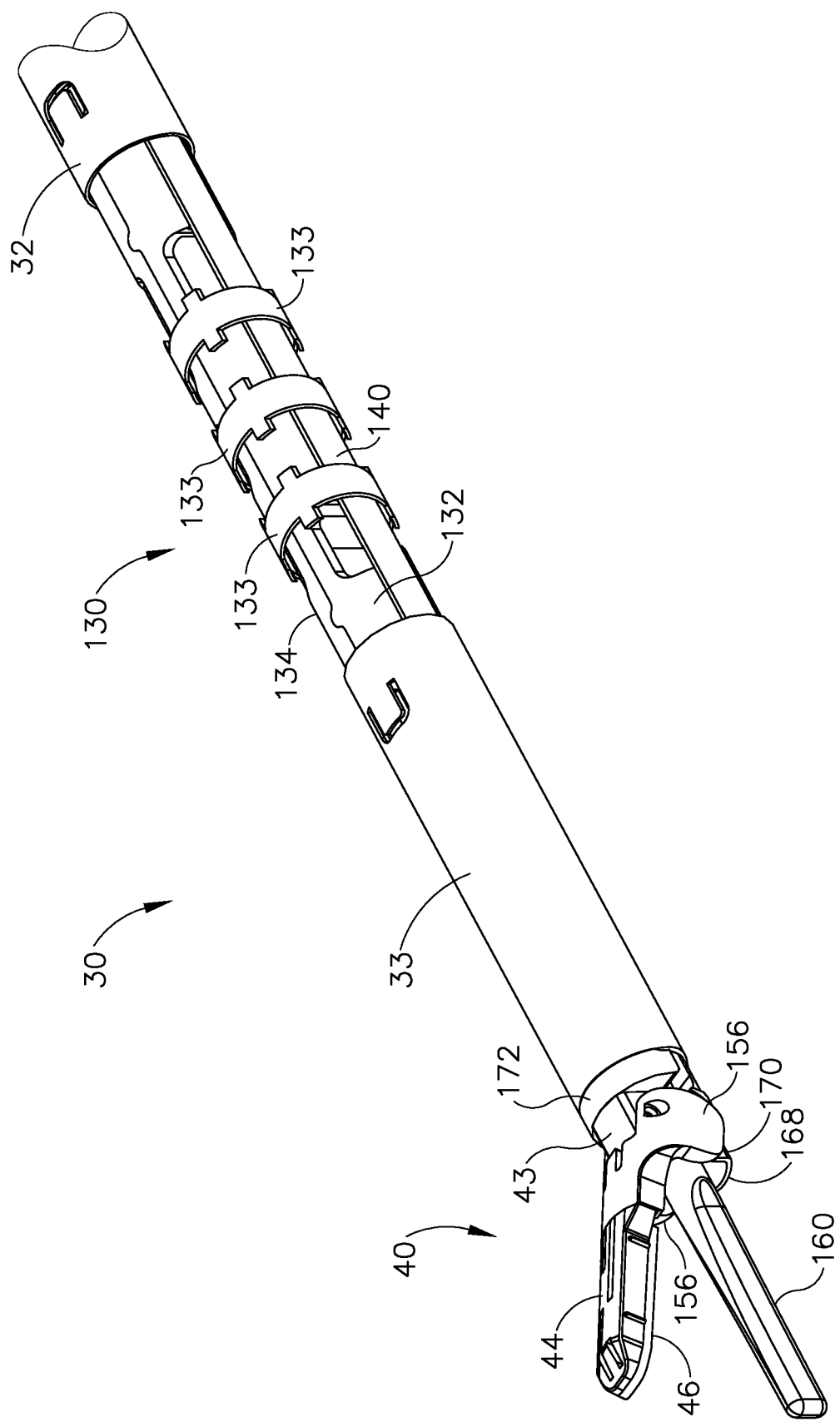
FIG. 2 depicts a perspective view of an articulation section of a shaft assembly and an end effector of the surgical instrument of FIG. 1.
Figure 3:
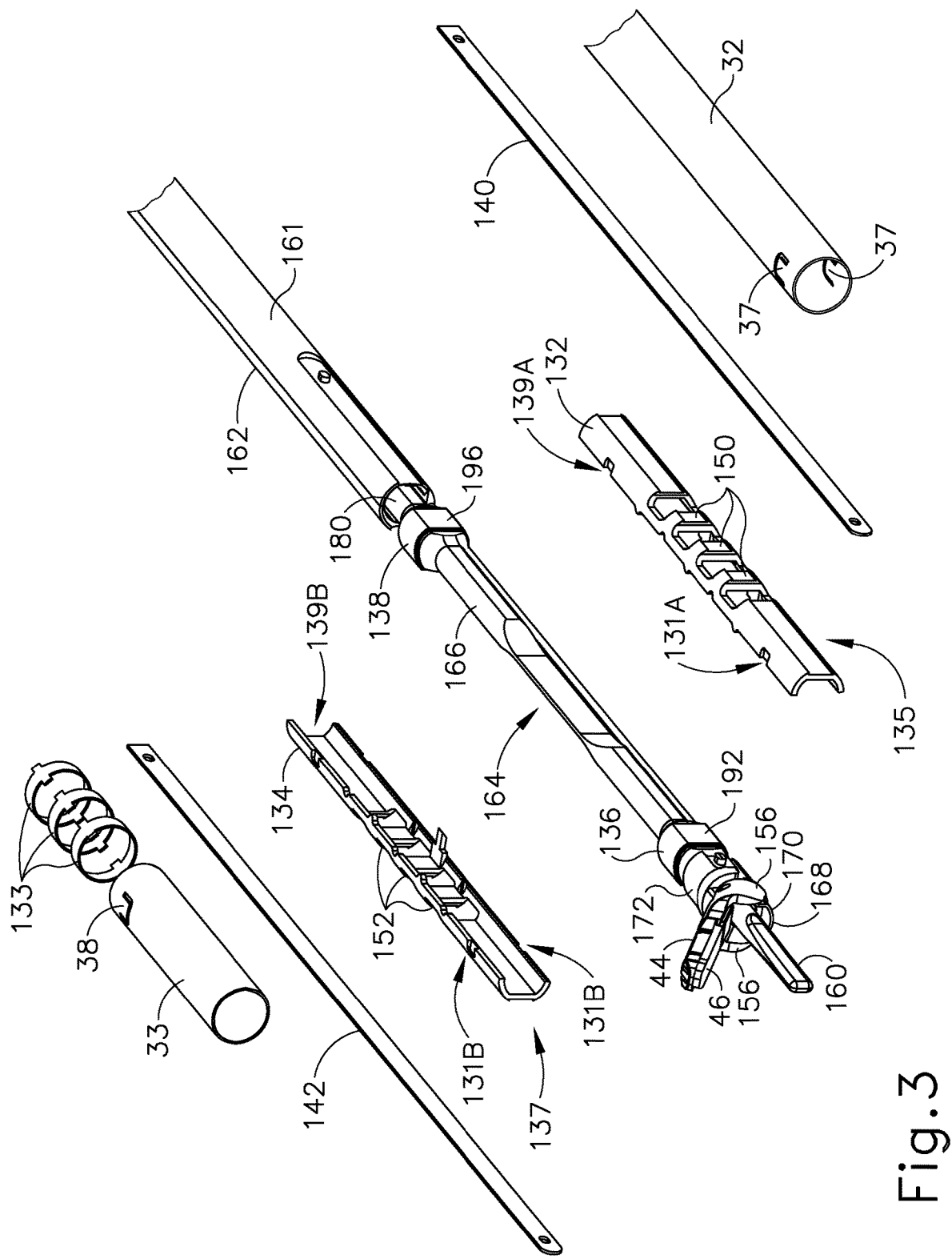
FIG. 3 depicts an exploded perspective view of an articulation section of the shaft assembly of FIG. 2.
Figure 4:
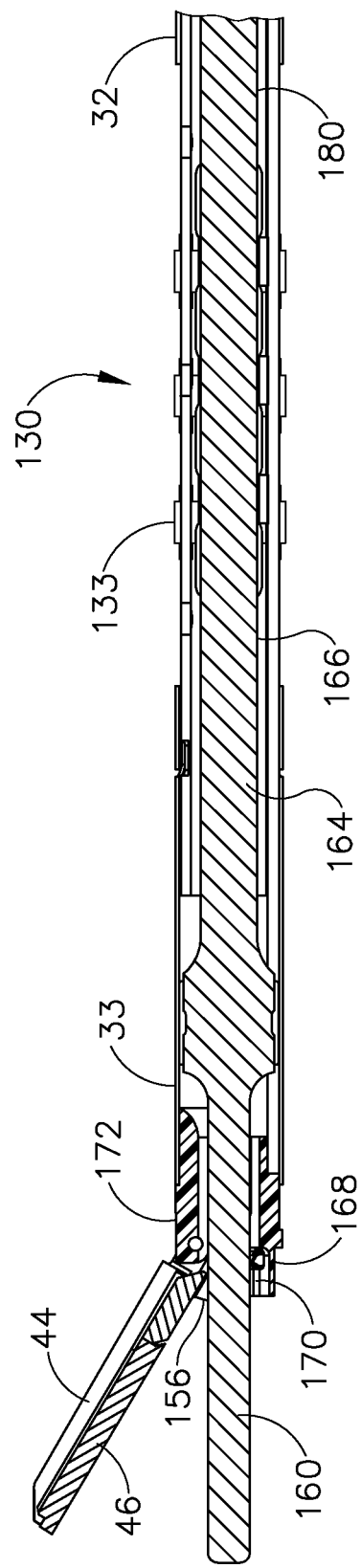
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

Figure 7:
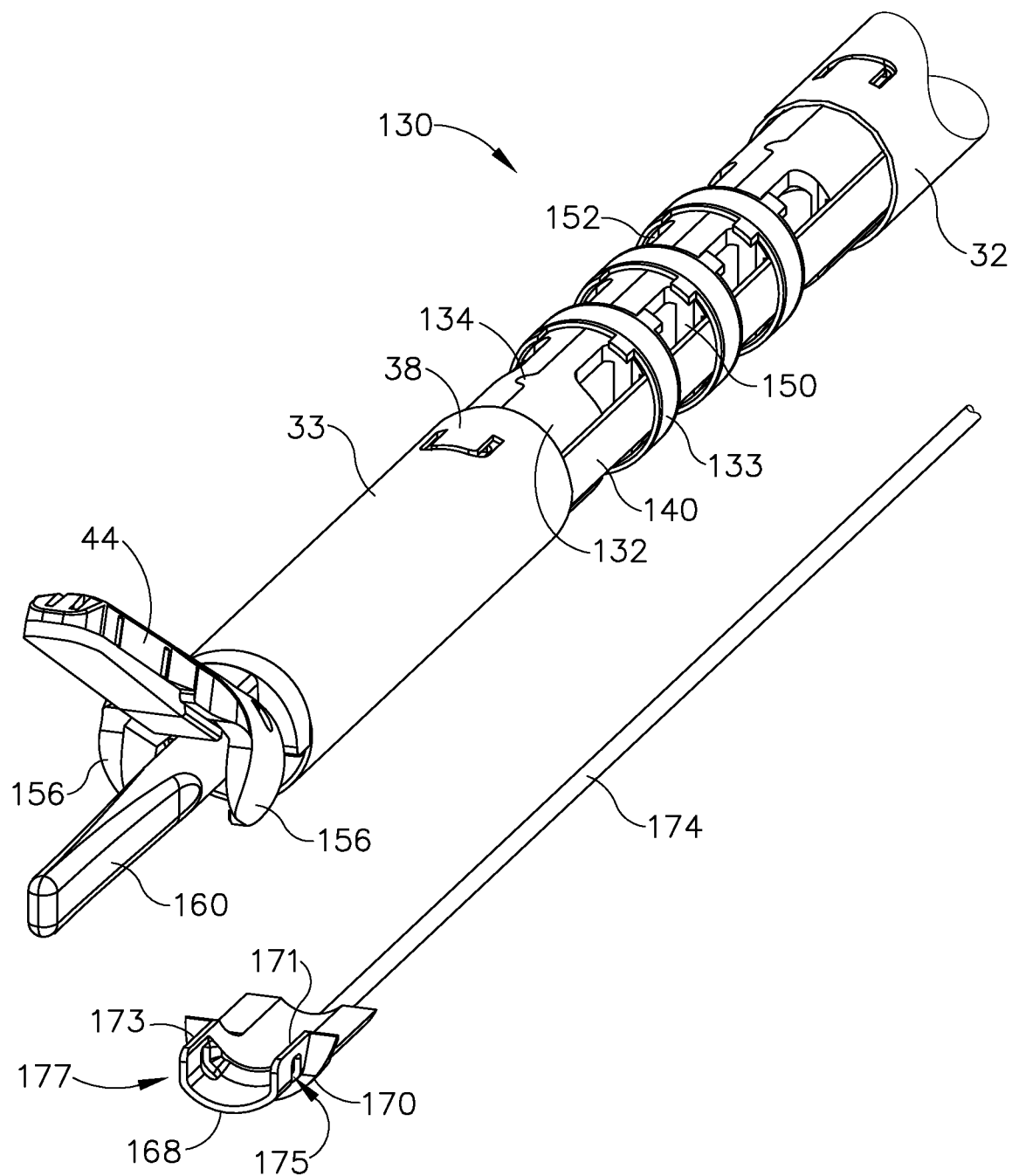
FIG. 7 depicts a partially exploded perspective view of the shaft assembly and end effector of FIG. 2.
Figure 8:
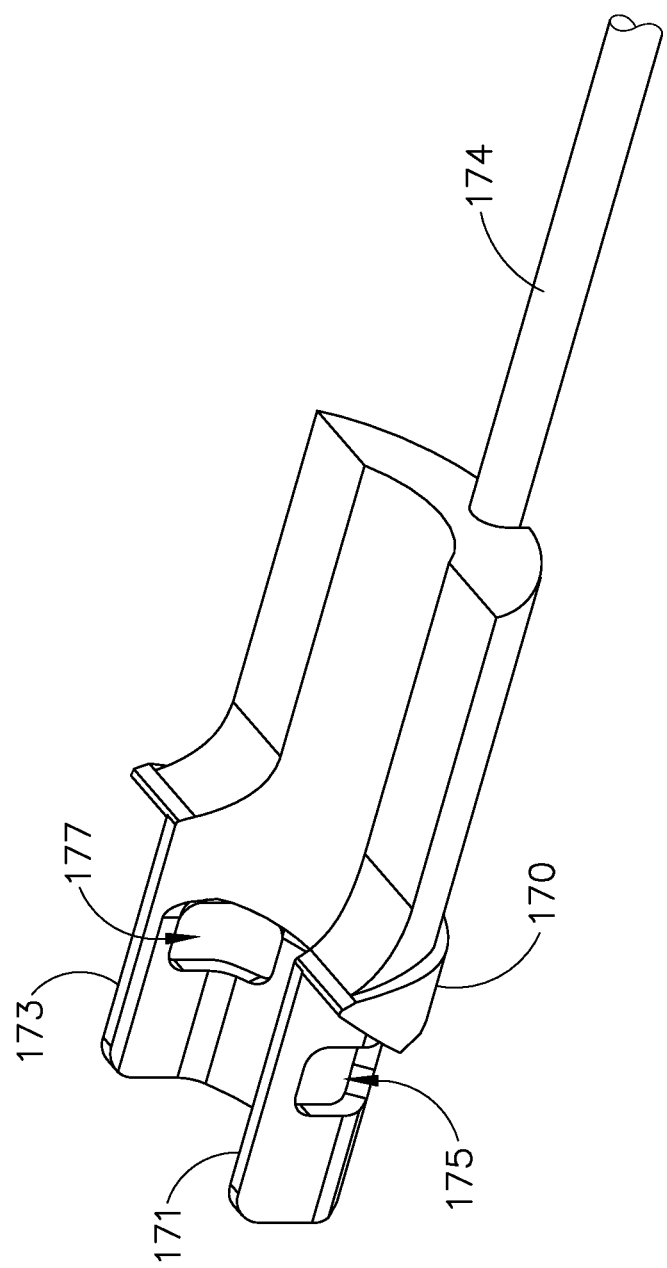
FIG. 8 depicts a perspective view of a distal collar and a drive cable of the shaft assembly of FIG. 2.

As best seen in FIGS. 7-8, a cable (174) is secured to lower distal shaft element (170). Cable (174) is operable to translate longitudinally relative to an articulation section (130) of shaft assembly (30) to selectively pivot clamp arm (44) toward and away from blade (160). In particular, cable (174) is coupled with trigger (28) such that cable (174)

translates proximally in response to pivoting of trigger (28) toward pistol grip (24), and such that clamp arm (44) thereby pivots toward blade (160) in response to pivoting of trigger (28) toward pistol grip (24). In addition, cable (174) translates distally in response to pivoting of trigger (28) away from pistol grip (24), such that clamp arm (44) pivots away from blade (160) in response to pivoting of trigger (28) away from pistol grip (24). Clamp arm (44) may be biased toward the open position, such that (at least in some instances) the operator may effectively open clamp arm (44) by releasing a grip on trigger (28).

Figure 10A:
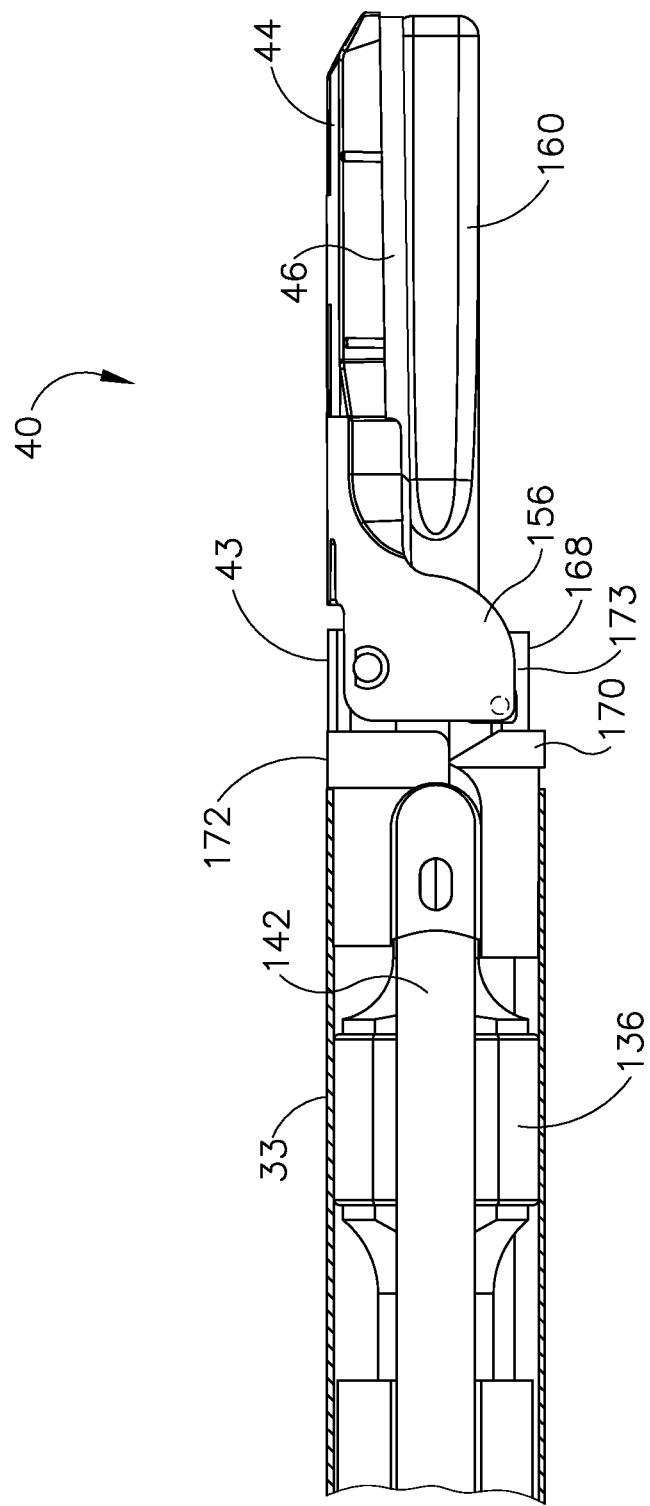
FIG. 10A depicts a side elevational view of the end effector and the distal portion of the shaft assembly of FIG. 2, with a clamp arm of the end effector in a closed position, and with an outer sheath shown in cross section to reveal components within the outer sheath.
Figure 10B:
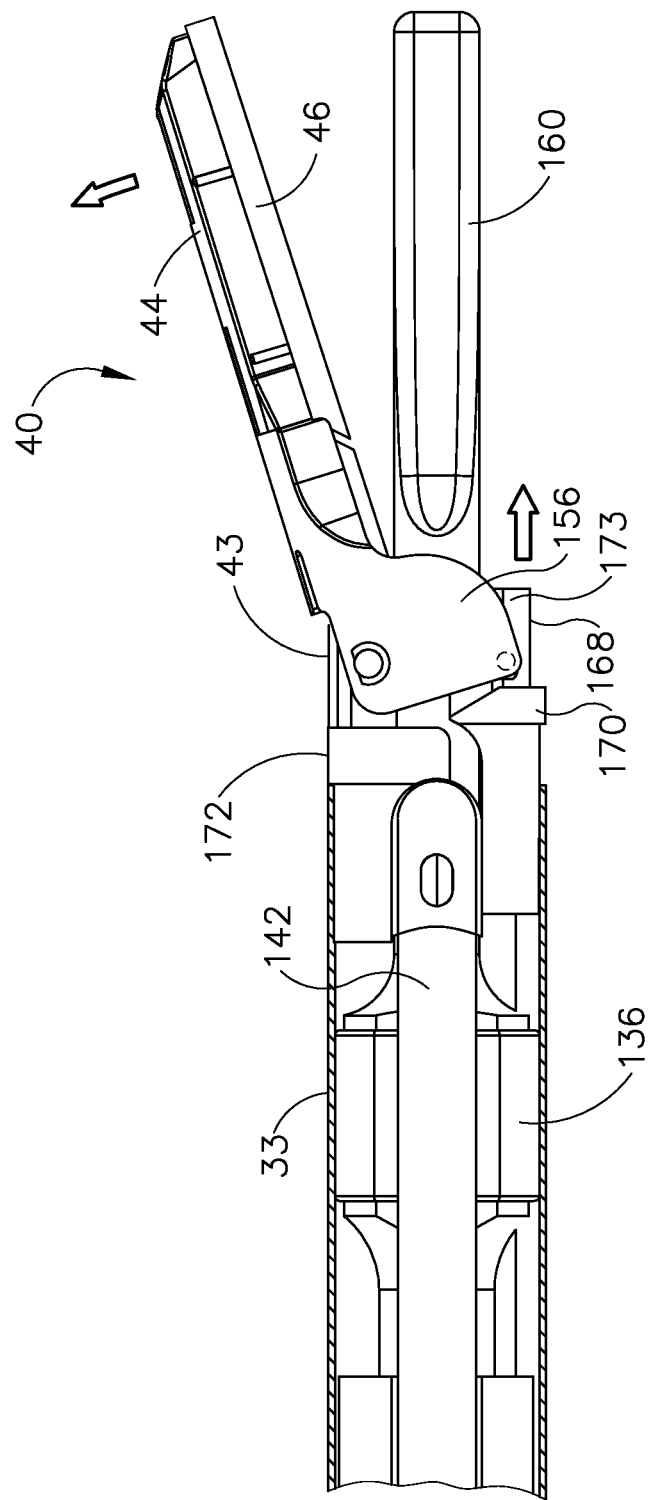
FIG. 10B depicts a side elevational view of the shaft assembly and end effector of FIG. 10A, with the clamp arm moved to a partially open position.
Figure 10C:
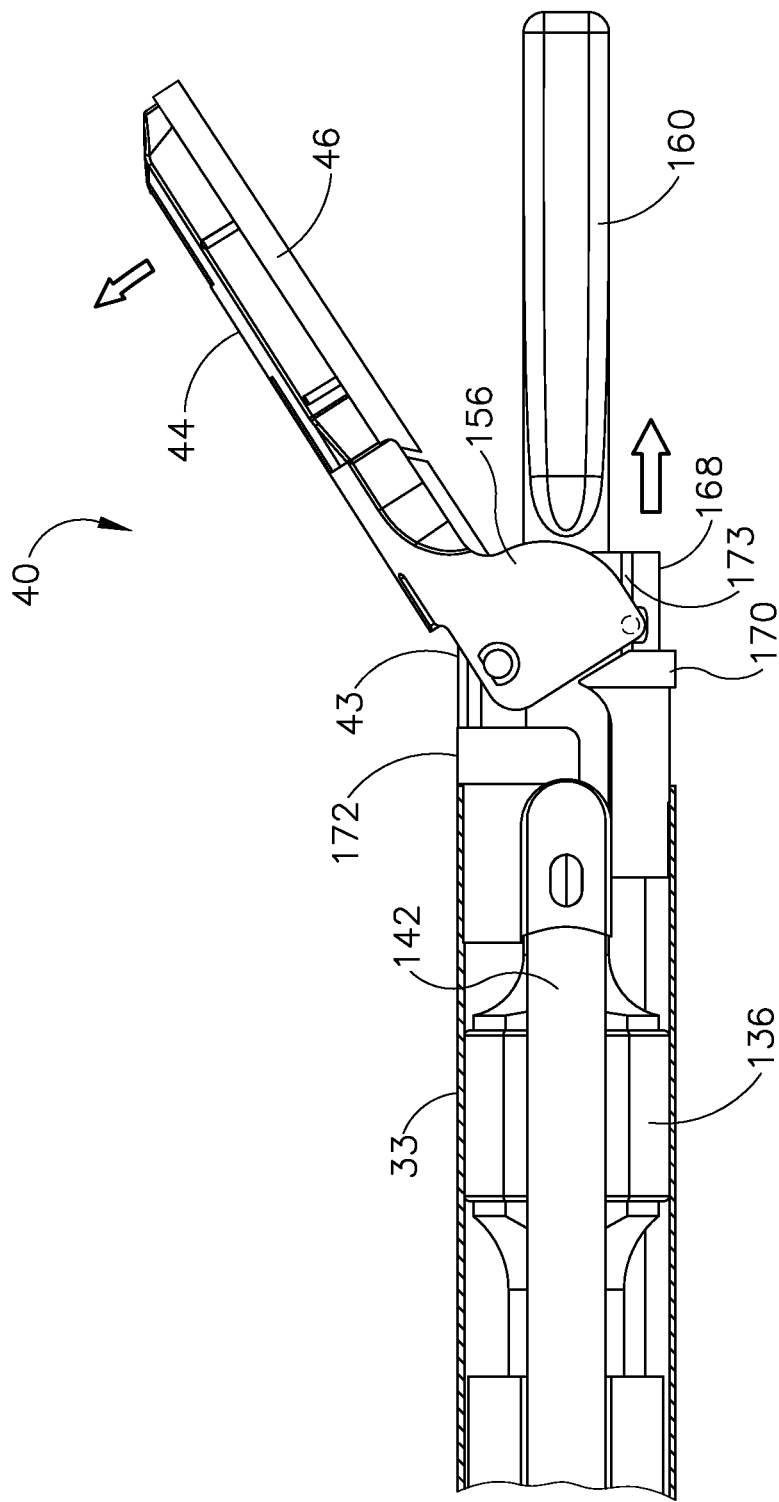
FIG. 10C depicts a side elevational view of the shaft assembly and end effector of FIG. 10A, with the clamp arm moved to a fully open position.

As shown in FIGS. 7-8, cable (174) is secured to a proximal end of lower distal shaft element (170). Lower distal shaft element (170) comprises a pair of distal flanges (171, 173) extending from a semi-circular base (168). Flanges (171, 173) each comprise a respective opening (175, 177). Clamp arm (44) is rotatably coupled to lower distal shaft element (170) via a pair of inwardly extending integral pins (41, 45). Pins (41, 45) extend inwardly from arms (156) of clamp arm (44) and are rotatably disposed within respective openings (175, 177) of lower distal shaft element (170). As shown in FIGS. 10A-10C, longitudinal translation of cable (174) causes longitudinal translation of lower distal shaft element (170) between a proximal position (FIG. 10A) and a distal position (FIG. 10C). Longitudinal translation of lower distal shaft element (170) causes rotation of clamp arm (44) between a closed position (FIG. 10A) and an open position (FIG. 10C).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). Transducer assembly (12) includes a set of piezoelectric discs (not shown) located proximal to a horn (not shown) of waveguide (180). The piezoelectric discs are operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

In the present example, the distal end of blade (160) is located at a position corresponding to an anti-node associated with resonant ultrasonic vibrations communicated through flexible portion (166) of waveguide (180), in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-7, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a knob (31) is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (130) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095, 367 on Aug. 4, 2015, the disclosures of which are incorporated by reference herein. Various other suitable forms that articulation section (130) may take will be apparent to those of ordinary skill in the art in view of the teachings herein.

As best seen in FIGS. 2-6B articulation section (130) of this example comprises a set of three retention collars (133) and a pair of ribbed body portions (132, 134), with a pair of articulation bands (140, 142) extending along respective channels (135, 137) defined between interior surfaces of retention collars (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

Figure 5:
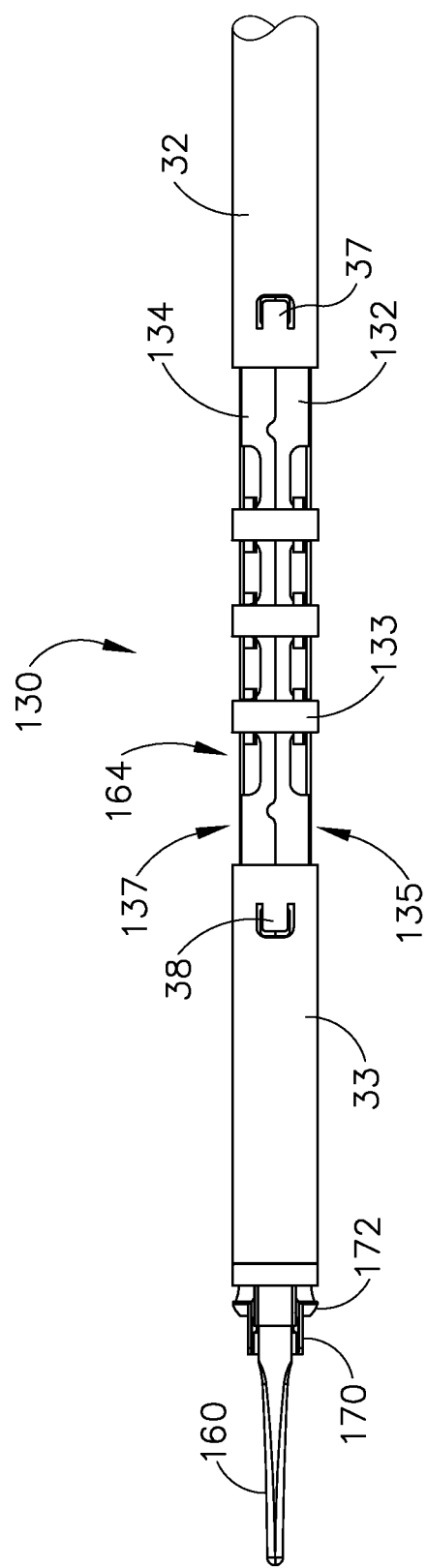
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
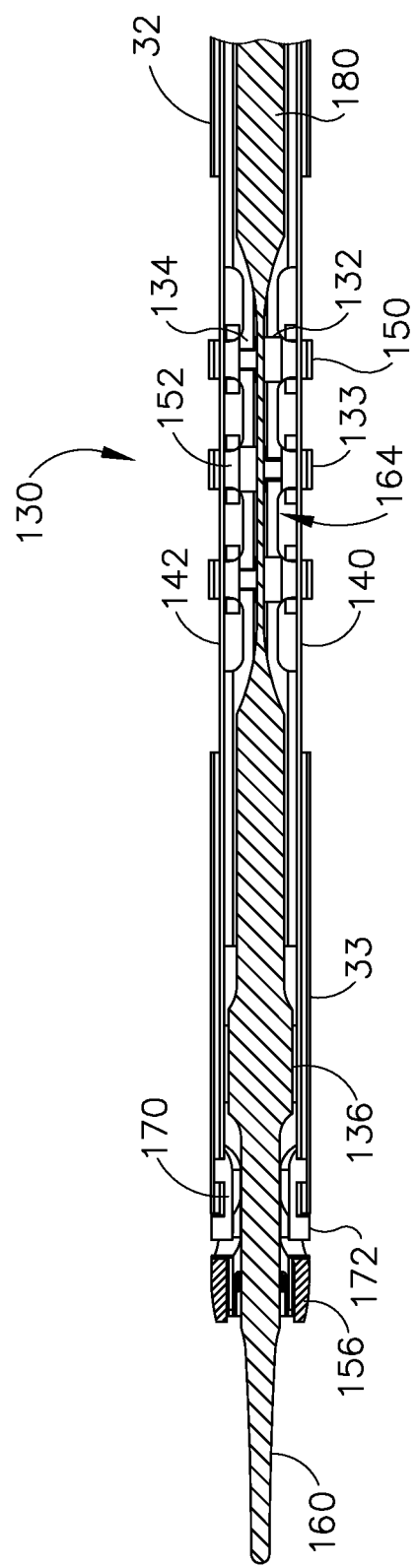
FIG. 6A depicts a cross-sectional top view of the shaft assembly and end effector of FIG. 2 in a straight configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to an articulated configuration as shown in FIG. 6B. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIG. 6B.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32): while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. patent application Ser. No. 13/868,336, entitled "Ultrasonic Device for Cutting and Coagulating," filed Apr. 23, 2013, issued as U.S. Pat. No. 10,238,416 on Mar. 2, 2019, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIG. 6B). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

As best seen in FIG. 9, an articulation control assembly (100) is secured to a proximal portion of outer sheath (32). Articulation control assembly (100) comprises a housing (110) and a rotatable knob (120). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163, 164) formed in top surfaces of translatable members (161, 162). Channels (163, 164) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121, 123). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In some versions of instrument (10), articulation section (130) of shaft assembly (30) is operable to achieve articulation angles up to between approximately 15° and approximately 30°, both relative to the longitudinal axis of shaft assembly (30) when shaft assembly (30) is in a straight (non-articulated) configuration. Alternatively, articulation section (130) may be operable to achieve any other suitable articulation angles.

In some versions of instrument (10), narrowed section (164) of waveguide (180) has a thickness between approximately 0.01 inches and approximately 0.02 inches. Alternatively, narrowed section (164) may have any other suitable thickness. Also in some versions, narrowed section (164) has a length of between approximately 0.4 inches and approximately 0.65 inches. Alternatively, narrowed section (164) may have any other suitable length. It should also be understood that the transition regions of waveguide (180) leading into and out of narrowed section (164) may be quarter rounded, tapered, or have any other suitable configuration.

In some versions of instrument (10), flanges (136, 138) each have a length between approximately 0.1 inches and approximately 0.2 inches. Alternatively, flanges (136, 138) may have any other suitable length. It should also be understood that the length of flange (136) may differ from the length of flange (138). Also in some versions, flanges (136, 138) each have a diameter between approximately 0.175 inches and approximately 0.2 inches. Alternatively, flanges (136, 138) may have any other suitable outer diameter. It should also be understood that the outer diameter of flange (136) may differ from the outer diameter of flange (138).

While the foregoing exemplary dimensions are provided in the context of instrument (10) as described above, it should be understood that the same dimensions may be used in any of the other examples described herein. It should also be understood that the foregoing exemplary dimensions are merely optional. Any other suitable dimensions may be used.

C. Exemplary Alternative Acoustic Waveguide with Curved Blade

FIGS. 11-13 show an exemplary alternative waveguide (280) that may be readily incorporated into instrument (10), particularly, into an acoustic drivetrain of instrument (10). Waveguide (280) of the present example includes a blade (260), which is operable to vibrate at ultrasonic frequencies in order to effectively cut through and seal tissue, particularly when the tissue is being compressed between blade (260) and another portion of an end effector, such as a curved version of clamp pad (46) of end effector (40). As best shown in FIG. 13, blade (260) is curved at a bend angle "O" relative to a longitudinal axis of waveguide (280).

In one example, the acoustic drivetrain includes transducer assembly (12) and acoustic waveguide (280). Acoustic waveguide (280) comprises a flexible portion (266). Transducer assembly (12) includes a set of piezoelectric discs (not shown) located proximal to a horn (not shown) of waveguide (280). The piezoelectric discs are operable to convert electrical power into ultrasonic vibrations, which are then transmitted along waveguide (280), including flexible portion (266) of waveguide (280), to blade (260) in accordance with known configurations and techniques. By way of example only, this portion of the acoustic drivetrain may be configured in accordance with various teachings of various references that are cited herein.

Flexible portion (266) of waveguide (280) includes a distal flange (236), a proximal flange (238), and a narrowed section (264) located between flanges (236, 238). Waveguide (280) includes longitudinally extending notches that are formed in the waveguide flanges to accommodate cable (274), which is discussed in more detail below. Cable is received in the lower notches (not shown); and the upper notches (237, 239) are formed to provide balance (i.e., to compensate for the presence of the lower notches). Waveguide (280) includes a tapered region (239) between distal flange (236) and blade (260). In the present example, flanges (236, 238) are located at positions corresponding to nodes associated with resonant ultrasonic vibrations communicated through waveguide (280). Narrowed section (264) is configured to allow flexible portion (266) of waveguide (280) to flex without significantly affecting the ability of flexible portion (266) of waveguide (280) to transmit ultrasonic vibrations. By way of example only, narrowed section (264) may be configured in accordance with one or more teachings of U.S. Pub. No. 2014/0005701 issued as U.S. Pat. No. 9,393,037 on Jul. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein.

It should be understood that waveguide (280) may be configured to amplify mechanical vibrations transmitted through waveguide (280). Furthermore, waveguide (280) may include features operable to control the gain of the longitudinal vibrations along waveguide (280) and/or features to tune waveguide (280) to the resonant frequency of the system. For example, as shown in FIG. 11, waveguide (280) includes a plurality of opposing pairs of longitudinally spaced, laterally presented notches (282a, 282b). In the present example, each notch (282a) of the three most proximal pairs of notches (282a) has a longer length than each notch (282b) of the two most distal pairs of notches (282b). Notches (282a, 282b) are provided, at least in part, to assist in controlling the vibratory properties of the waveguide (280), which are different in waveguide (280) than in waveguide (180) due in part to the curved configuration of blade (260). Various suitable ways in which waveguide (280) may be mechanically and acoustically coupled with transducer assembly (12) will be apparent to those of ordinary skill in the art in view of the teachings herein.

Each flange (236, 238) of waveguide (280) includes a respective pair of opposing, laterally presented flats (292, 296). Flats (292, 296) are oriented along vertical planes that are parallel to a vertical plane extending through narrowed section (264) of flexible portion (266). Flats (296) are configured to provide clearance for articulation bands (212, 214). In particular, flats (296) of proximal flange (238) accommodate articulation bands (214) between proximal flange (138) and the inner diameter of proximal outer sheath (204). Notably, articulation bands (212, 214) are coupled to waveguide (280) at a point proximal to distal flange (236). Of course, flats (292, 296) could be substituted with a variety of features, including but not limited to slots, channels, etc., with any suitable kind of profile (e.g., square, flat, round, etc.). In the present example, flats (292, 296) are formed in a milling process, though it should be understood that any other suitable process(es) may be used. Various suitable alternative configurations and methods of forming flats (292, 296) will be apparent to those of ordinary skill in the art in view of the teachings herein. It should also be understood that waveguide (280) may include flats formed in accordance with at least some of the teachings of U.S. Pub. No. 2013/0289592, entitled "Ultrasonic Device for Cutting and Coagulating," published Oct. 31, 2013, issued as U.S. Pat. No. 10,238,416 on Mar. 26, 2019, the disclosure of which is incorporated by reference herein.

In the present example, the distal end of blade (260) is located at a position corresponding to an anti-node associated with resonant ultrasonic vibrations communicated through flexible portion (266) of waveguide (280), in order to tune the acoustic assembly to a preferred resonant frequency $f_o$ when the acoustic assembly is not loaded by tissue. When transducer assembly (12) is energized, the distal end of blade (260) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (280) to reach blade (260), thereby providing oscillation of blade (260) at the resonant ultrasonic frequency. Thus, when tissue is secured between blade (260) and a curved version of clamp pad (46), for example, the ultrasonic oscillation of blade (260) may simultaneously sever the tissue and denature the proteins in adjacent tissue cells, thereby providing a coagulative effect with relatively little thermal spread. In some versions, an electrical current may also be provided through blade (260) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, various suitable ways in which waveguide (280) may be configured will be apparent to those of ordinary skill in the art in view of the teachings herein.

D. Exemplary Alternative End Effector and Shaft Assembly with One-Way Articulation FIGS. 14-16 and 32A-33B show an exemplary alternative shaft assembly (200) and end effector (240) that may be readily incorporated into instrument (10). In the example shown, shaft assembly (200) and end effector are configured to accommodate for the properties of curved blade (260), as discussed in more detail below. Shaft assembly (200) of this example comprises a distal outer sheath (202), a proximal outer sheath (204), and a plurality of flex rings (206) that form a portion of an articulation section (210). While articulation section (130) is configured to articulate in two lateral directions relative to the longitudinal axis of shaft assembly (30), articulation section (210) of the present example is configured to articulate in only one direction relative to a longitudinal axis of shaft assembly (200). Particularly, in the present example, articulation section (210) is allowed to articulate in one lateral direction, but is substantially prevented from articulating in the opposite lateral direction.

Articulation section (210) is operable to selectively position end effector (240) at various lateral deflection angles, in one direction, relative to a longitudinal axis defined by proximal outer sheath (204). In the present example, the direction in which articulation section (210) is permitted to articulate is the same direction which curved blade (260) bends away from the axis (at bend angle (A)). End effector (240) includes blade (260) and a pivoting clamp arm (244) having a clamp pad (245). In the present example, clamp arm (244) and clamp pad (245) are curved at a bend angle that is substantially similar to the bend angle (A) of blade (260). End effector (240) is configured to operate substantially similar to end effector (40) discussed above except for the differences discussed below. In particular, clamp arm (244) of end effector (240) is operable to compress tissue against blade (260). When blade (260) is activated while clamp arm (244) compresses tissue against blade (260), end effector (240) simultaneously severs the tissue and denatures the proteins in adjacent tissue cells, thereby providing a coagulative effect.

Figure 15:
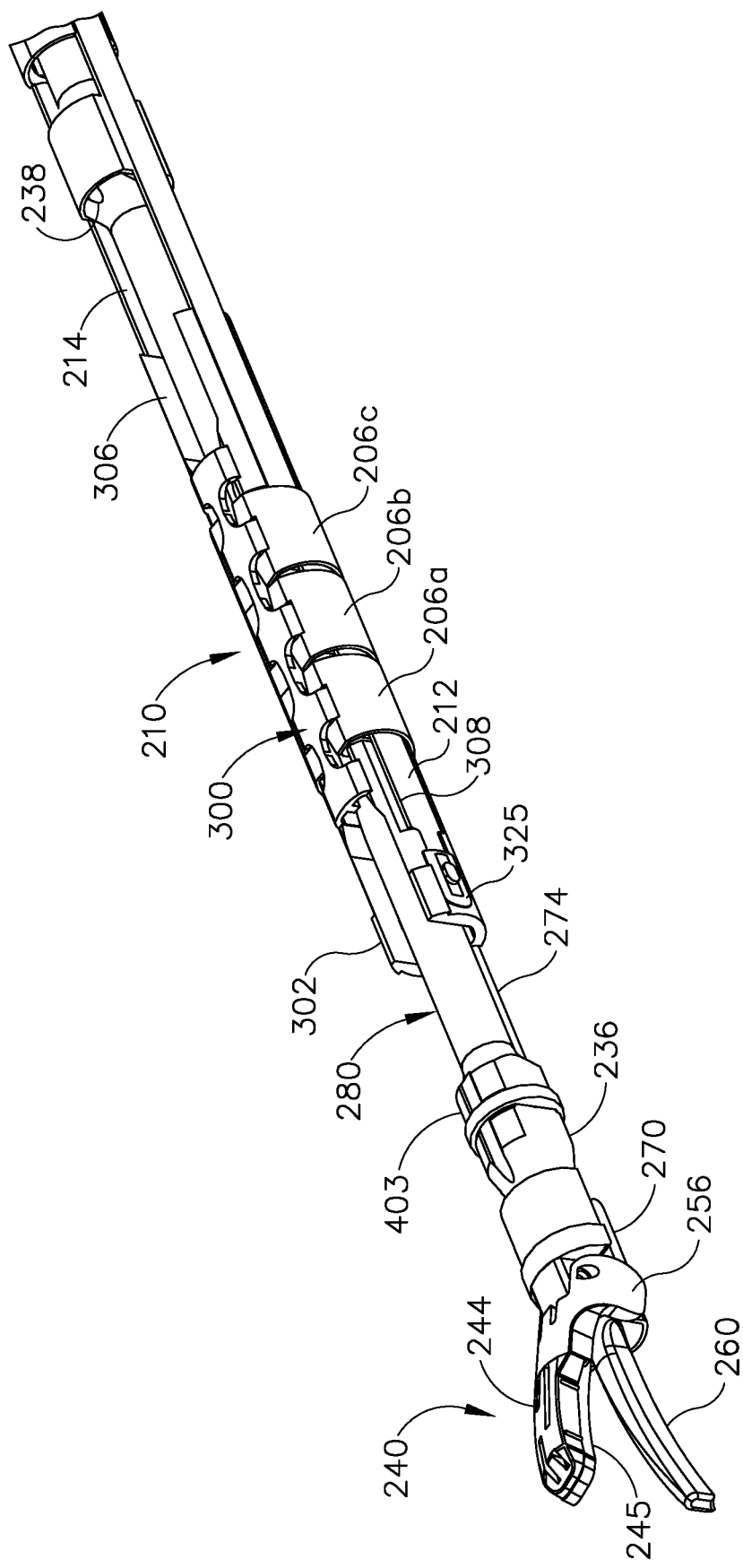
FIG. 15 depicts a perspective view of the articulation section of the shaft assembly and the end effector of FIG. 14, with certain parts omitted to show details.
Figure 16:
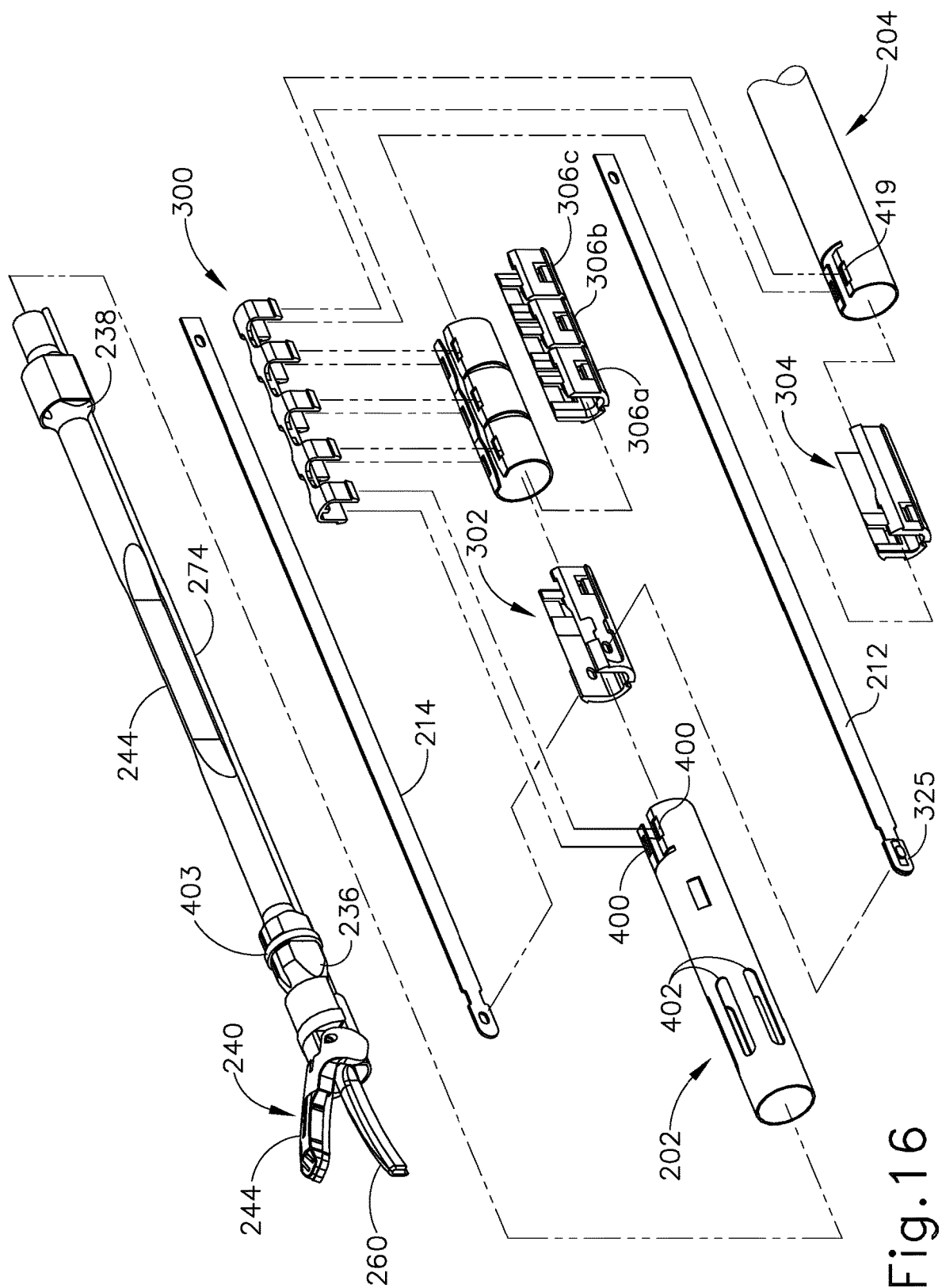
FIG. 16 depicts an exploded perspective view of the articulation section of the shaft assembly and the end effector of FIG. 14.

Clamp arm (244) is operable to selectively pivot toward and away from blade (242) to selectively clamp tissue between clamp pad (245) and blade (260), in a manner substantially similar to clamp arm (44). Clamp arm (244) is coupled to a trigger (e.g., trigger (28)) such that clamp arm (244) is pivotable toward ultrasonic blade (260) in response to pivoting of trigger (28) toward pistol grip (24); and such that clamp arm (244) is pivotable away from ultrasonic blade (260) in response to pivoting of trigger (28) away from pistol grip (24). As best seen in FIGS. 15-16, a cable (274) is secured to a lower distal shaft element (270). Cable (274) is operable to translate longitudinally relative to an articulation section (210) of shaft assembly (200) to selectively pivot clamp arm (244) toward and away from blade (260). In particular, cable (274) is coupled with trigger (28) such that cable (274) translates proximally in response to pivoting of trigger (28) toward pistol grip (24), and such that clamp arm (244) thereby pivots toward blade (260) in response to pivoting of trigger (28) toward pistol grip (24). In addition, cable (274) translates distally in response to pivoting of trigger (28) away from pistol grip (24), such that clamp arm (244) pivots away from blade (260) in response to pivoting of trigger (28) away from pistol grip (24). Clamp arm (244) may be biased toward the open position, such that (at least in some instances) the operator may effectively open clamp arm (244) by releasing a grip on trigger (28). Various suitable ways in which clamp arm (244) may be coupled with trigger (28) will be apparent to those of ordinary skill in the art in view of the teachings herein.

In the example shown, cable (274) is secured to a proximal end of a lower distal shaft element (270), which is configured in a manner substantially similar to lower distal shaft element (170). In that regard, lower distal shaft element (270) comprises a pair of distal flanges (not shown) extending from a semi-circular base. The flanges each comprise a respective opening (not shown). Clamp arm (244) is rotatably coupled to lower distal shaft element (270) via a pair of inwardly extending integral pins (not shown). The pins extend inwardly from arms (256) of clamp arm (244) and are rotatably disposed within respective openings of lower distal shaft element (270). In a manner similar to that shown in FIGS. 10A-C, longitudinal translation of cable (274) causes longitudinal translation of lower distal shaft element (270) between a proximal position and a distal position. Longitudinal translation of lower distal shaft element (270) causes rotation of clamp arm (244) between a closed position and an open position.

Shaft assembly (200) further comprises a pair of articulation bands (212, 214). Distal ends of articulation bands (212, 214) are secured to distal flex member (302) of articulation section (210). Articulation bands (212, 214) are configured to operate substantially similar to articulation bands (140, 142) discussed above except for the differences discussed below. In particular, as shown best in FIGS. 32A-33B, articulation bands (212, 214) are permitted to cause articulation of articulation section (210) in substantially only one direction, as discussed in more detailed below. When articulation bands (212, 214) are translated longitudinally in an opposing fashion, a moment is created and applied to distal flex member (302) and also distal outer sheath (202), and also to other components of the articulation section (210) due to the operable coupling among the distal flex member (302), distal outer sheath (202), and other components of articulation section (210). This causes articulation section (210) and narrowed section (249) of flexible portion (248) of waveguide (280) to articulate, without transferring axial forces in articulation bands (212, 214) to waveguide (246).

Figure 14:
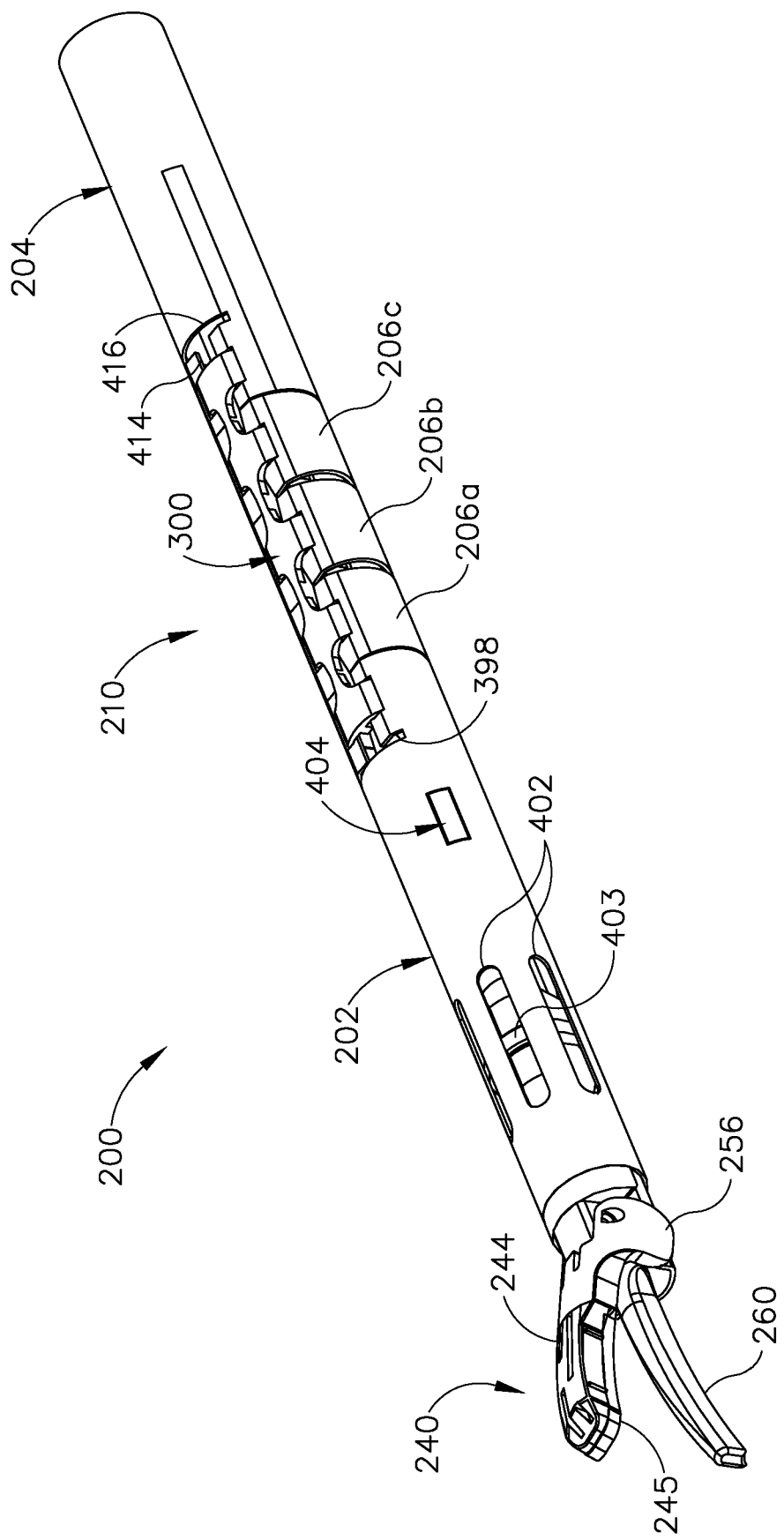
FIG. 14 depicts a perspective view of an exemplary alternative articulation section of a shaft assembly and an end effector incorporating the waveguide of FIG. 11, which is suitable for incorporation into the surgical instrument of FIG. 1.

As shown in FIGS. 14-16, articulation section (210) comprises a distal flex member (302), a proximal flex member (304), and a plurality of flex base members (306a-c). Articulation section (210) further comprises distal outer sheath (202), a proximal outer sheath (204), and flex rings (206a-c). Articulation section (210) also includes a flexible collar (300) that is configured to operably couple certain components of the articulation section (210) to one another, as discussed in more detail below. Distal flex member (302) t is operably coupled to the distal ends of a respective articulation band (212, 214). Flex base members (304a-c) are positioned proximally relative to the distal flex member (302), and proximal flex member (304) positioned proximal of flex base members (306a-c). Distal flex member (302), proximal flex member (304), and flex base members (306a-c) collectively define opposing channels (308, 310) for receiving articulation bands (212, 214), respectively.

Figure 17:
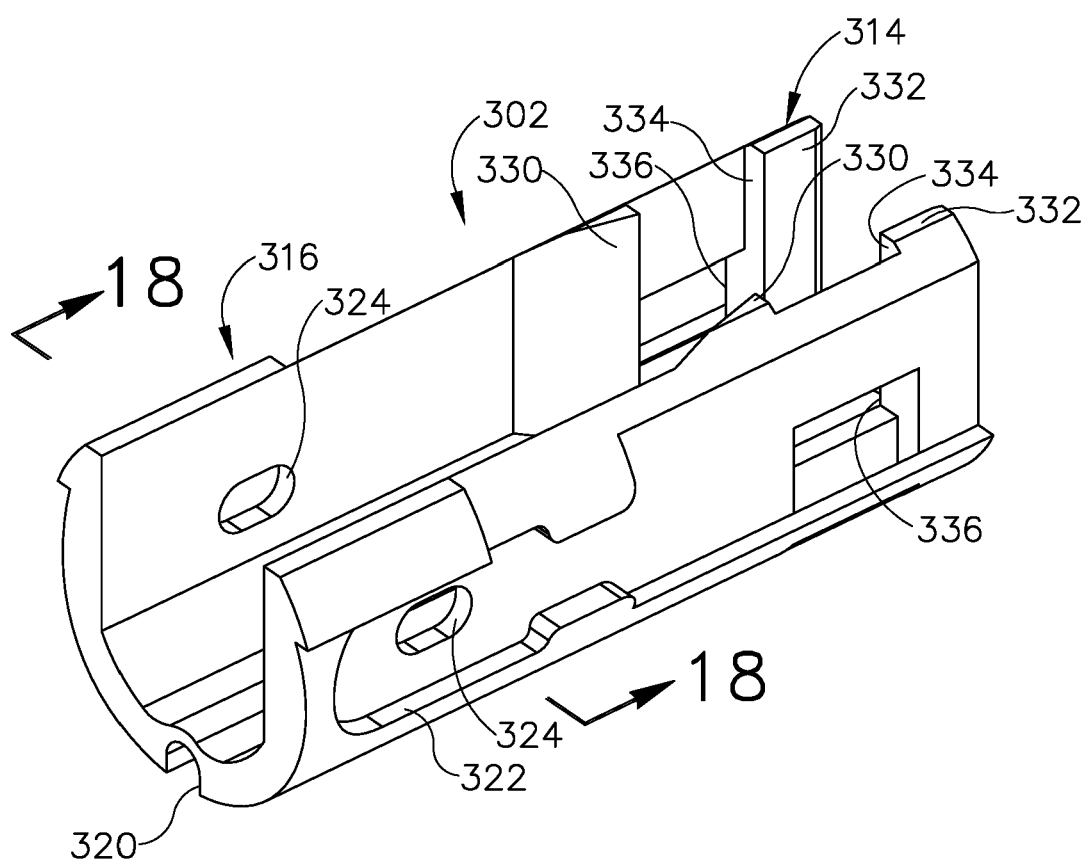
FIG. 17 depicts a perspective view of a distal flex member of the articulation section of FIG. 14.
Figure 18:
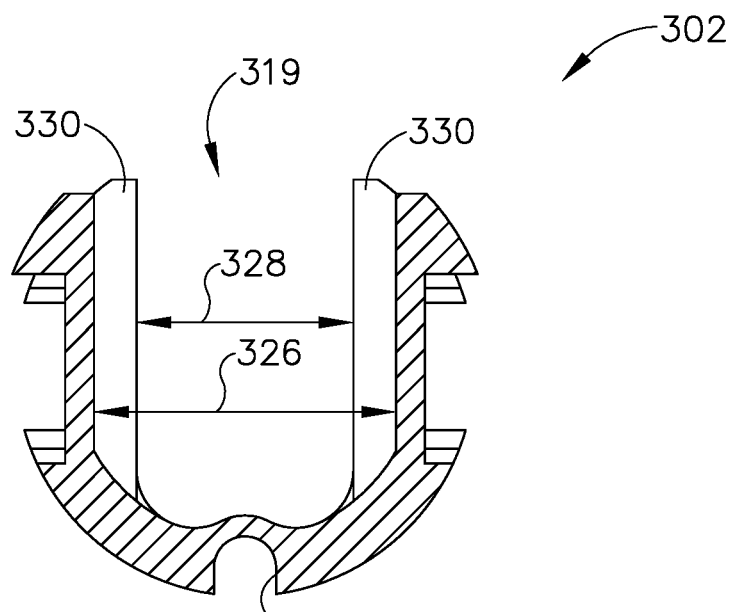
FIG. 18 depicts a cross-sectional view of the distal flex member of FIG. 17, taken along line 18-18 of FIG. 17.

FIGS. 17-18 show distal flex member (302) of the present example in more detail. As shown, distal flex member (302) includes a proximal end (314), a distal end (316), and a generally U-shaped body (318) that defines a space (319) configured for receiving at least a portion of waveguide (280). A bottom portion of distal flex member (302) includes a longitudinally extending recess (320) that is configured to receive cable (274). Each side of distal flex member (302) includes a channel (322) that is shaped and configured for receiving a distal end of a respective articulation band (212, 214). Each channel (322) includes an aperture (324) that is configured to receive a portion of a fastener (325) (FIG. 15) for coupling a respective articulation band (212, 214) to a side of the distal flex member (302). By way of example only, fastener (325) may comprise a pin, a rivet, and/or any other suitable kind of structure.

Space (319) for receiving waveguide (280) includes a first dimensioned portion (326) that receives a distal portion of waveguide and a second dimensioned portion (328), which includes a smaller dimension than first dimensioned portion (326). Second dimensioned portion (328) is configured to receive narrowed section (264) of waveguide (280). Notably, however, distal flex member (302) does not contact waveguide (280). Second dimensioned portion (326) is defined by a pair of opposing angled flanges (330) which extend radially inwardly toward a central longitudinal axis of distal flex member (302). Angled flanges (330) define a tapered transition portion between the first dimensioned portion (326) and second dimensioned portion (328). Second dimensioned portion (328) is further defined by a pair of flanges (332), which also extend radially inwardly toward the central longitudinal axis of distal flex member (302), at the proximal end (314) of distal flex member (302). Flanges (330, 332) define a pair of opposing slots (334) that extend along a plane that is parallel to the longitudinal axis of distal flex member. Each slot (334) includes an aperture (336). Various suitable ways in which distal flex member (302) may be configured will be apparent to those of ordinary skill in the art in view of the teachings herein.

Figure 19:
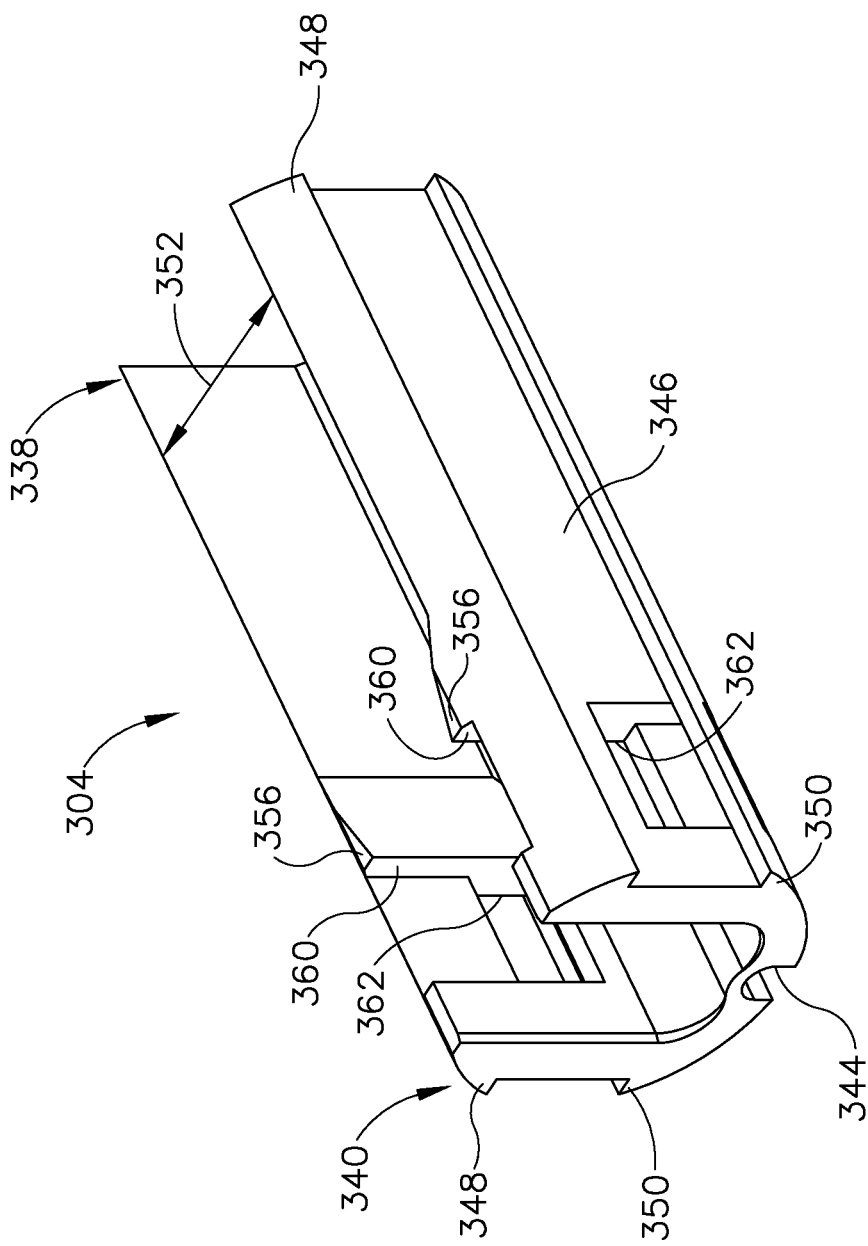
FIG. 19 depicts a perspective view of a proximal flex member of the articulation section of FIG. 14.
Figure 20:
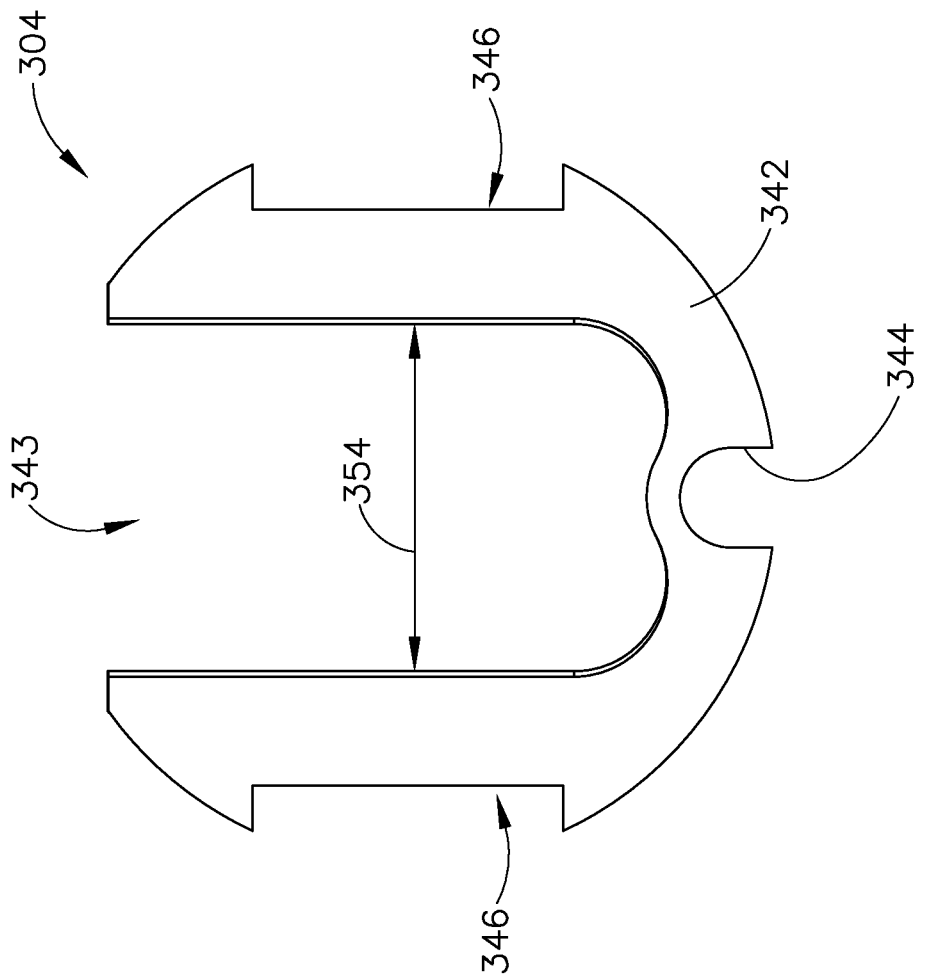
FIG. 20 depicts a front elevational view of the proximal flex member of FIG. 19.
Figure 21:
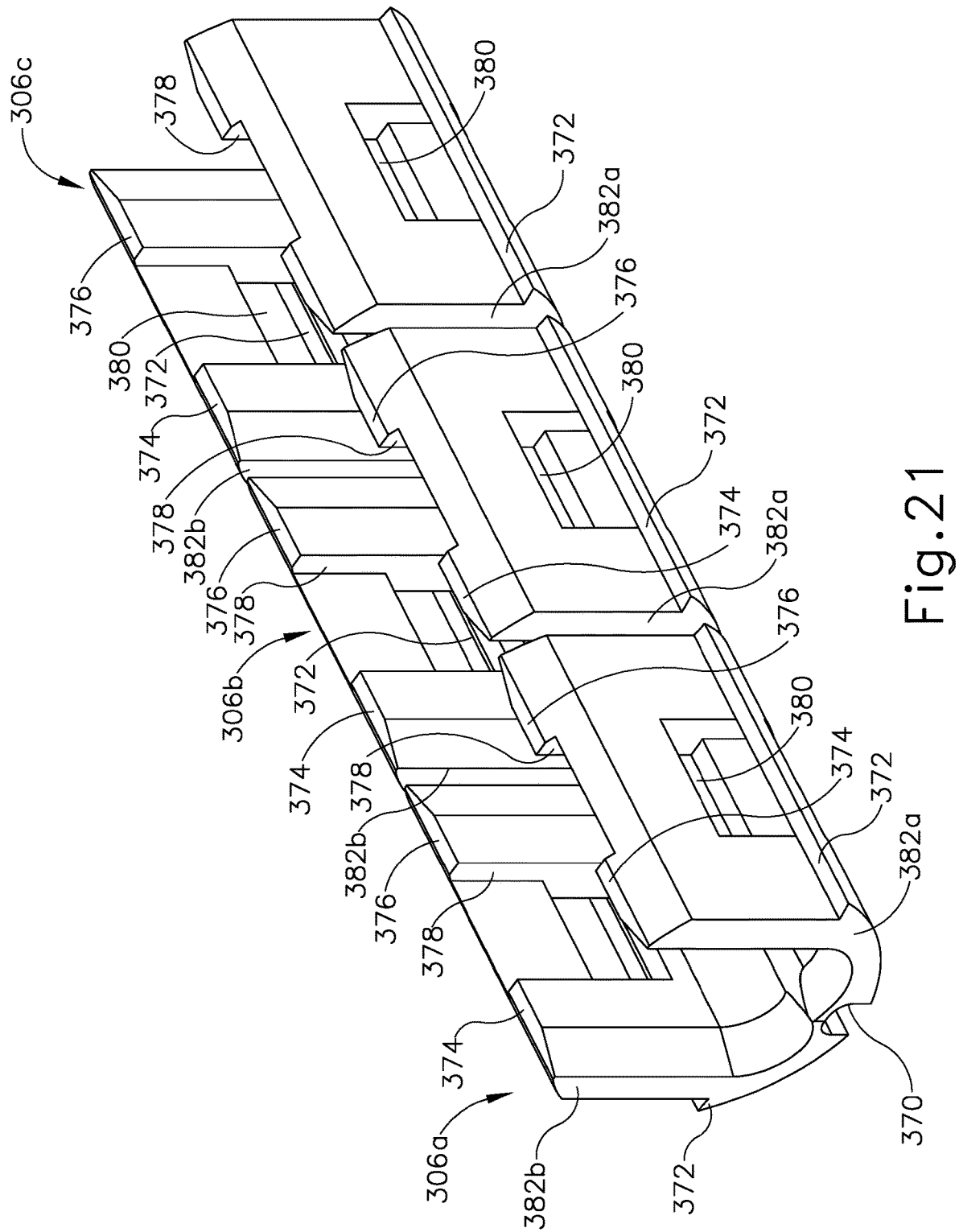
FIG. 21 depicts a perspective view of a plurality of flex base members of the articulation section of FIG. 14, in an unflexed configuration.
Figure 22:
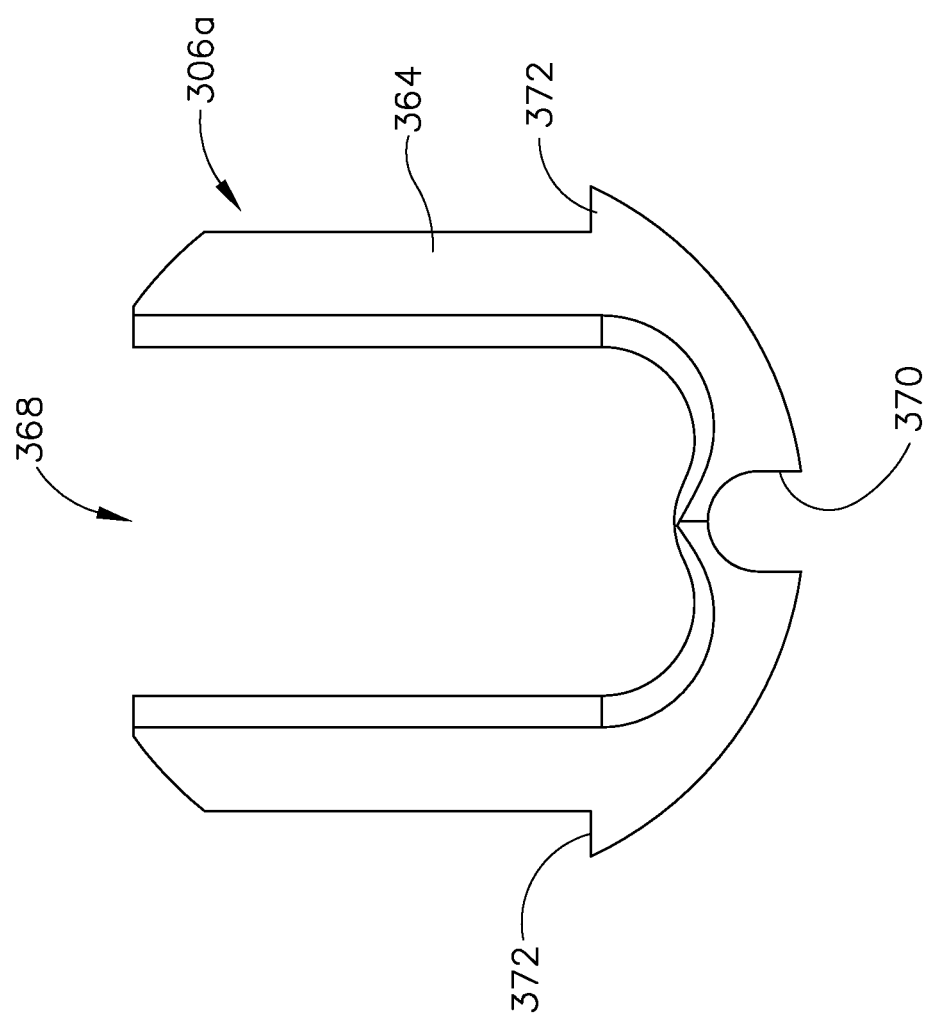
FIG. 22 depicts a front elevational view of the plurality of flex base members of FIG. 21.

FIGS. 19-20 show proximal flex member (304) of the present example in more detail. As shown, proximal flex member (304) includes a proximal end (338), a distal end (340) and a generally U-shaped body (342) that defines a space (343) configured for receiving at least a portion of waveguide (280). A bottom portion of proximal flex member (302) includes a longitudinal recess (344) that is configured to receive cable (274). Each side of proximal flex member (304) includes a channel (346) that is shaped and configured for receiving portion of a respective articulation band (212, 214) (and which forms a portion of channels (308, 310)). Each channel (346) is defined in part by an upper, shelf (348) and a lower shelf (350).

The space (343) of proximal flex member (304) for receiving waveguide (280) includes a first dimensioned portion (352) that receives a portion of waveguide (280) and a second dimensioned portion (354), which includes a smaller dimension than first dimensioned portion (326). Second dimensioned portion (354) is configured to receive narrowed section (264) of waveguide (280), though proximal flex member (304) does not contact waveguide (280). Second dimensioned portion (354) is defined by a pair of opposing angled flanges (356) which extend radially inwardly toward a central longitudinal axis of proximal flex member (304). Angled flanges (356) define a tapered transition portion between the first dimensioned portion (352) and second dimensioned portion (354). Second dimensioned portion (354) is further defined by a pair of flanges (358), which also extend radially inwardly toward the central longitudinal axis of proximal flex member (304), at the distal end (340) of proximal flex member (304). Flanges (356, 358) define a pair of opposing slots (360). Each slot (360) includes a generally rectangular aperture (362). Various suitable ways in which proximal flex member (304) may be configured will be apparent to those of ordinary skill in the art in view of the teachings herein.

Flex base members (306a-c), as shown in more detail in FIGS. 21-23B, define a single, unitary body (364) comprising three members (306a-c), with living hinges (366) between adjoining members (306a-c). However, in other examples, flex base members (306a-c) may be separate, individual members. In the example shown, body (364) is generally U-shaped and defines a space (368) configured for receiving at least a portion of waveguide (280). However, body (364) does not contact waveguide (280). A bottom portion of each flex base member (306a-c) includes a longitudinal recess (370) configured to receive cable (274). Each side of each base member (306a-c) includes a radially outwardly extending shelf (372), each of which defines a boundary on each side of the base members (306a-c) for receiving a portion of a respective articulation band (212, 214). Each base member (306a-c) includes a respective pair of opposing distal flanges (374) and a respective pair of opposing proximal flanges (376) extending radially inwardly toward a central longitudinal axis of body (364). The distal and proximal flanges (374, 376) in each pair of flanges (374, 376) define a slot (378) therebetween. Each slot (378) includes a generally rectangular aperture (380).

Each base member (306a-c) includes a respective first distal face portion (382a), a second distal face portion (382b), a first proximal face portion (384a), and a second proximal face portion (384b). As shown best in FIG. 23B, base members (306a-c) are configured to transition to a flexed position from an unflexed position (FIG. 23A) when, for example, articulation bands (212, 214) are moved longitudinally relative to one another. In the unflexed position, there is a gap between adjacent first proximal and distal faces (384a, 382a); and between second proximal and distal faces (384b, 382b). First distal faces (382a) and second distal faces (382b) are disposed at an oblique angle ($\theta_{23A\text{-}1}$) relative to an imaginary plane that is perpendicular to the longitudinal axis of base members (306a-c). First proximal edges (384a) and first proximal edges (384b) are disposed at an oblique angle ($\theta_{23A\text{-}2}$) relative to an imaginary plane that is perpendicular to the longitudinal axis of base members (306a-c). In the present example, angle ($\theta_{23A\text{-}1}$) and angle ($\theta_{23A\text{-}2}$) are substantially equal. Thus, the angle between adjacent first proximal and distal edges (384a, 382a) in an unflexed position; and between adjacent second proximal and distal edges (384b, 382b) in an unflexed position, is $\theta_{23A\text{-}1}+\theta_{23A\text{-}2}$.

Figure 23A:
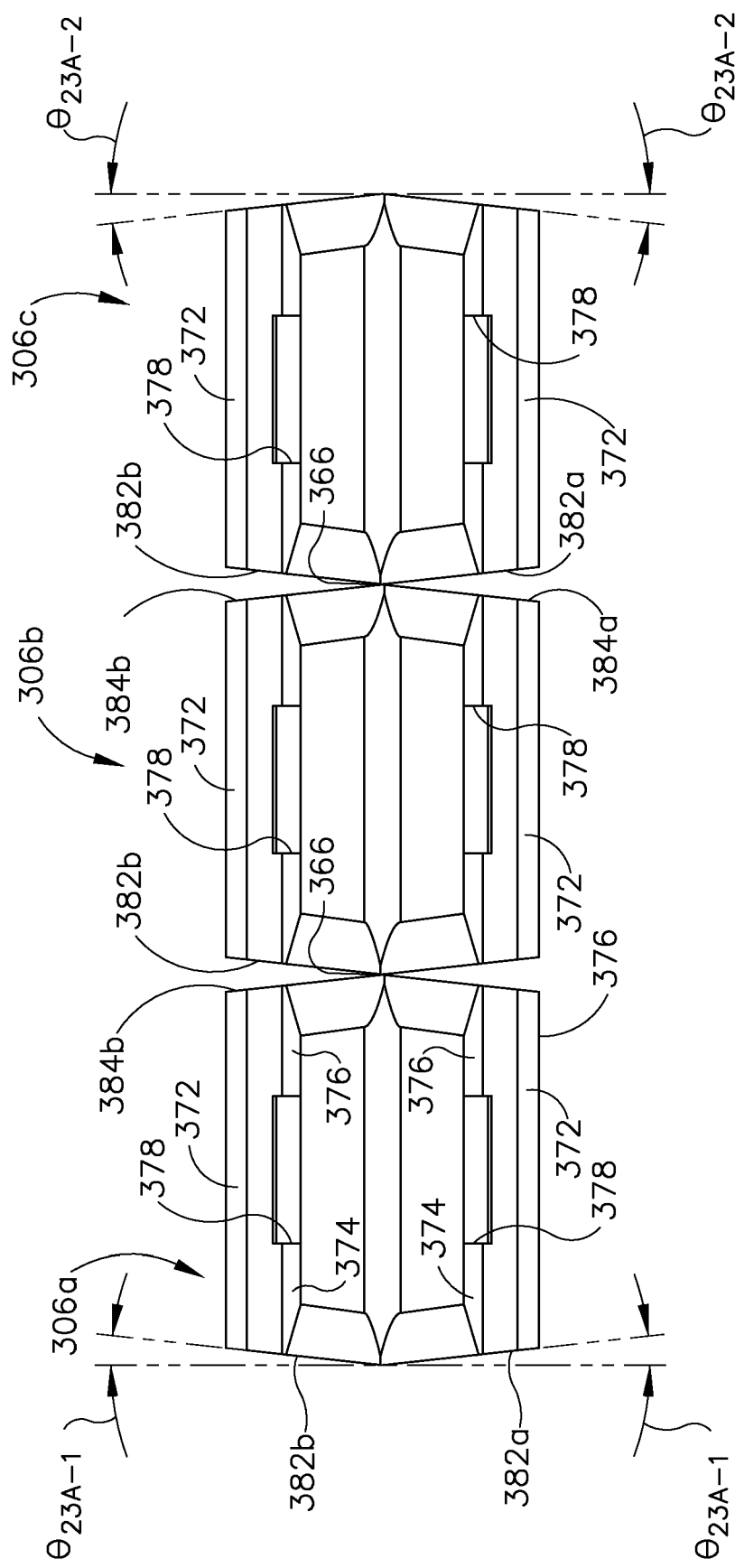
FIG. 23A depicts a top elevational view of the plurality of flex base members of FIG. 21, in an unflexed configuration.
Figure 23B:
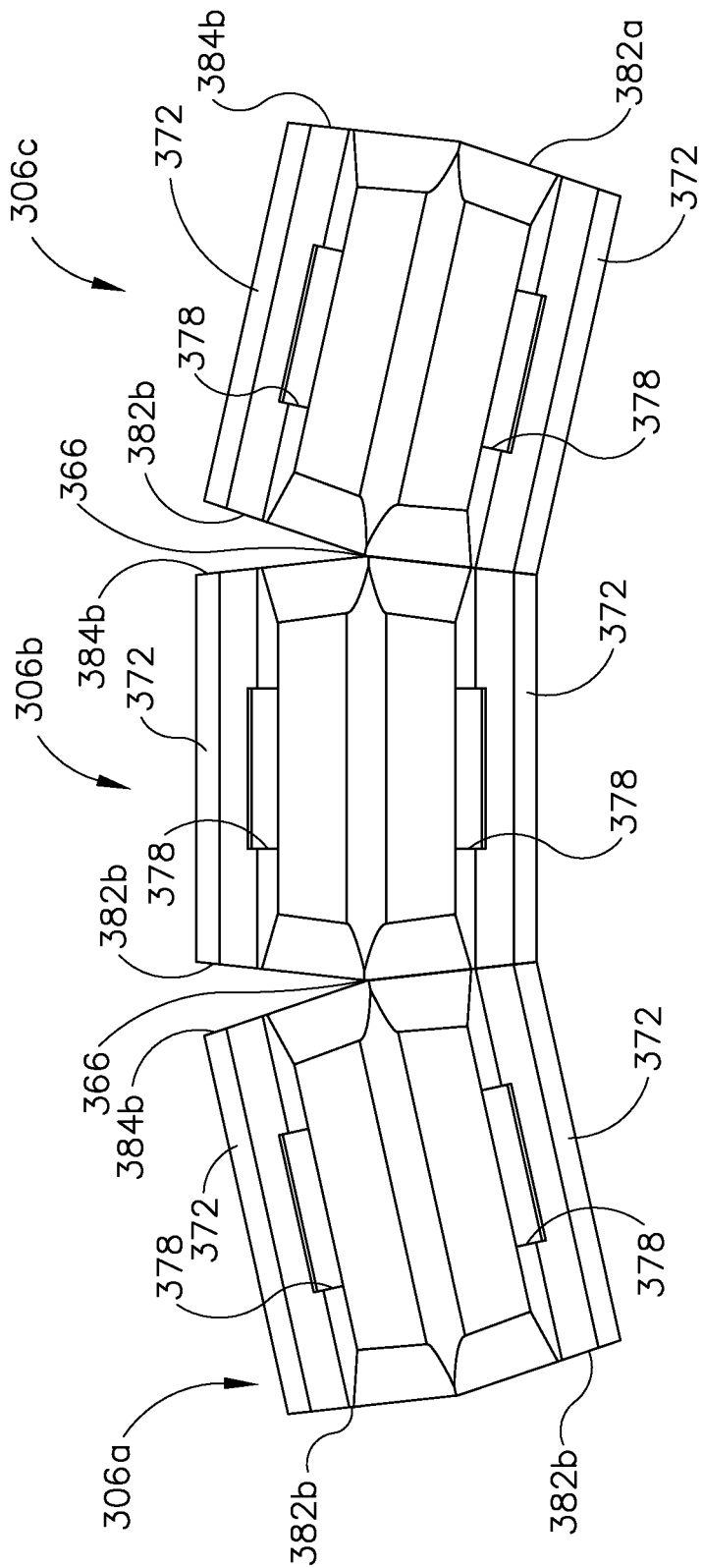
FIG. 23B depicts a top elevational view of the flex base members of FIG. 21, in a flexed configuration.
Figure 24:
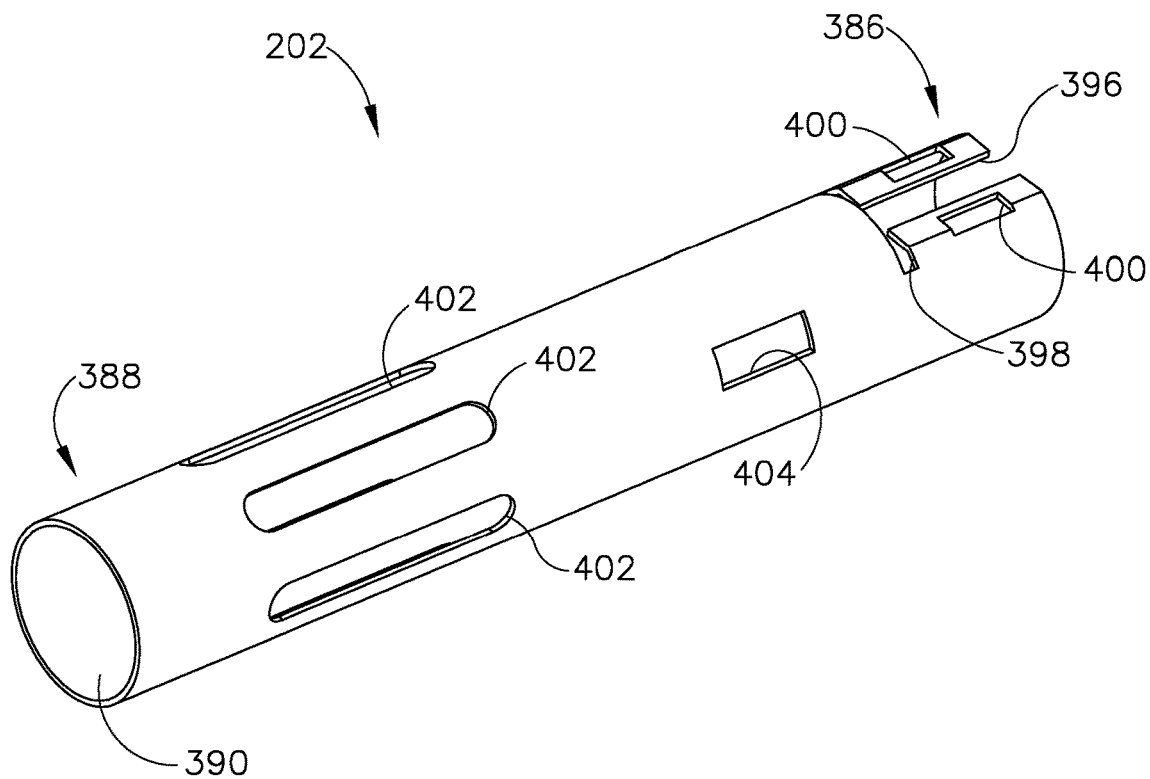
FIG. 24 depicts a perspective view of a distal tube member of the articulation section of FIG. 14.
Figure 25:
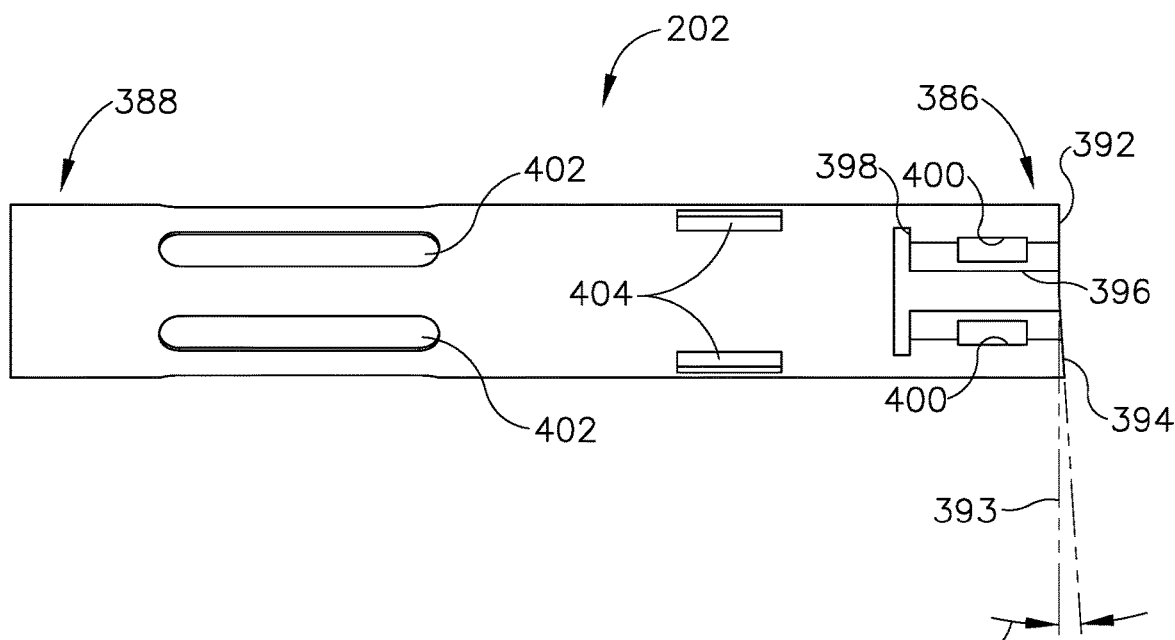
FIG. 25 depicts a top elevational view of the distal tube member of FIG. 24.
Figure 26:
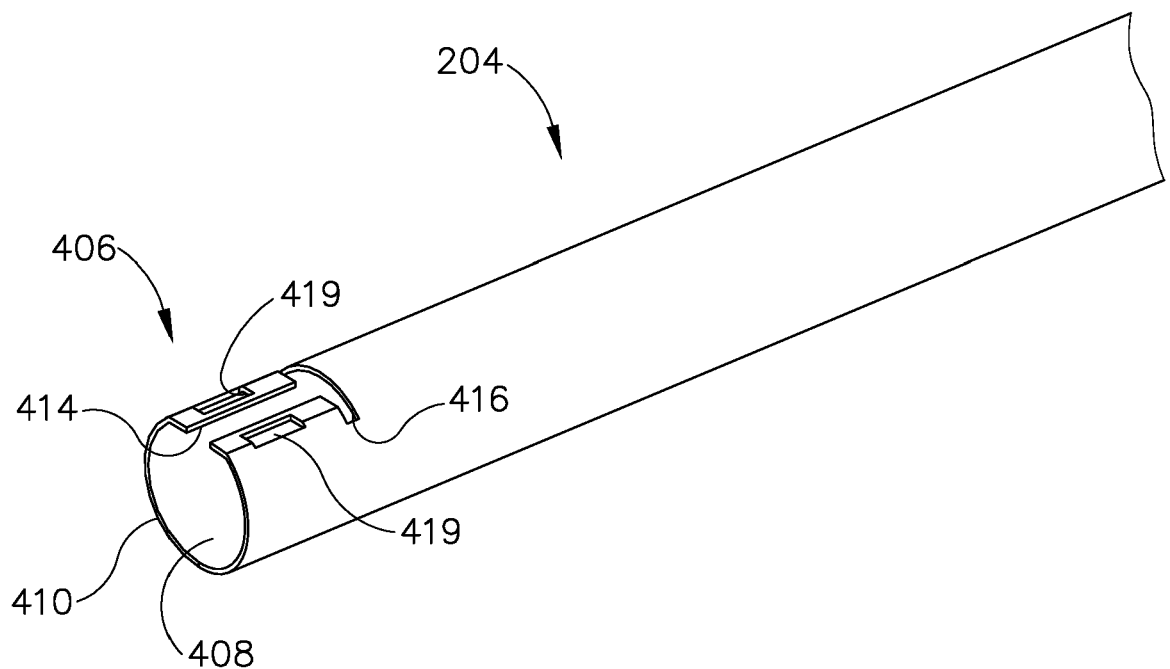
FIG. 26 depicts a perspective view of a proximal tube member of the articulation section of FIG. 14.

As shown in FIG. 23B, base members (306a-c) are in a flexed position after pivoting in one direction relative to a central longitudinal axis about living hinges (366), such that first proximal faces (384a) substantially abut respective first distal faces (382a) of an adjoining base member (306a-c). It will be understood that in some versions, base members (306a-c) may pivot in an opposite direction, for example, such that second proximal faces (382b) substantially abut respective second distal faces (382b) of an adjoining base member (306a-c). However, in the present example, as will be understood from the discussion below, other components of articulation section (210) may effectively allow base members (306a-c) to pivot in only one direction. Various suitable ways in which flex base members (306a-c) may be configured will be apparent to those of ordinary skill in the art in view of the teachings herein.

Still referring to FIGS. 14-16, articulation section (210) of the present example also includes a distal outer sheath (202), a proximal outer sheath (204), and flex rings (206a-c) that at least partially surround other components of articulation section (210). Referring also to FIGS. 24-25 and 33A-34B, distal outer sheath (202) of the present example more particularly comprises a proximal end (386), a distal end (388), and a lumen (390) extending therebetween. At least a first portion (392) of a proximal edge of distal outer sheath (202) extends along an imaginary plane (393) that is perpendicular to the longitudinal axis of distal outer sheath (202), while a second portion (394) of proximal edge extends at angle ($\theta_{25}$) relative to plane (393). Distal outer sheath (202) of the present example further comprises a longitudinal channel (396) extending from the proximal edge (392) in a direction parallel to a longitudinal axis of distal outer sheath (202). Longitudinal channel (396) terminates at a transverse channel (398). Transverse channel (398) of the present example extends parallel to the plane (393) but perpendicular to longitudinal channel (396).

Distal outer sheath (202) is coupled to waveguide (280) via an elastomeric ring (403), which is positioned about distal flange (236) of waveguide (280). Thus, as discussed in more detail below, when distal outer sheath (202) is laterally deflected by the articulation of articulation section (210), distal outer sheath (202) transfers that lateral deflection to waveguide (280), thereby articulating end effector (240).

Distal outer sheath (202) of the present example further comprises a pair of apertures (400), which are generally rectangular in shape, and spaced laterally from one another and from longitudinal cutout (396). Distal outer sheath (202) further includes a plurality of circumferentially spaced obround apertures (402). As shown, in the present example, there are six obround apertures (402), but in other examples, there may be more or less than six obround apertures (402). Longitudinally between obround apertures (402) and proximal end (386), distal tube member includes a pair of angularly spaced, generally rectangular apertures (404). Various suitable ways in which distal outer sheath (202) may be configured will be apparent to those of ordinary skill in the art in view of the teachings herein.

Figure 27:
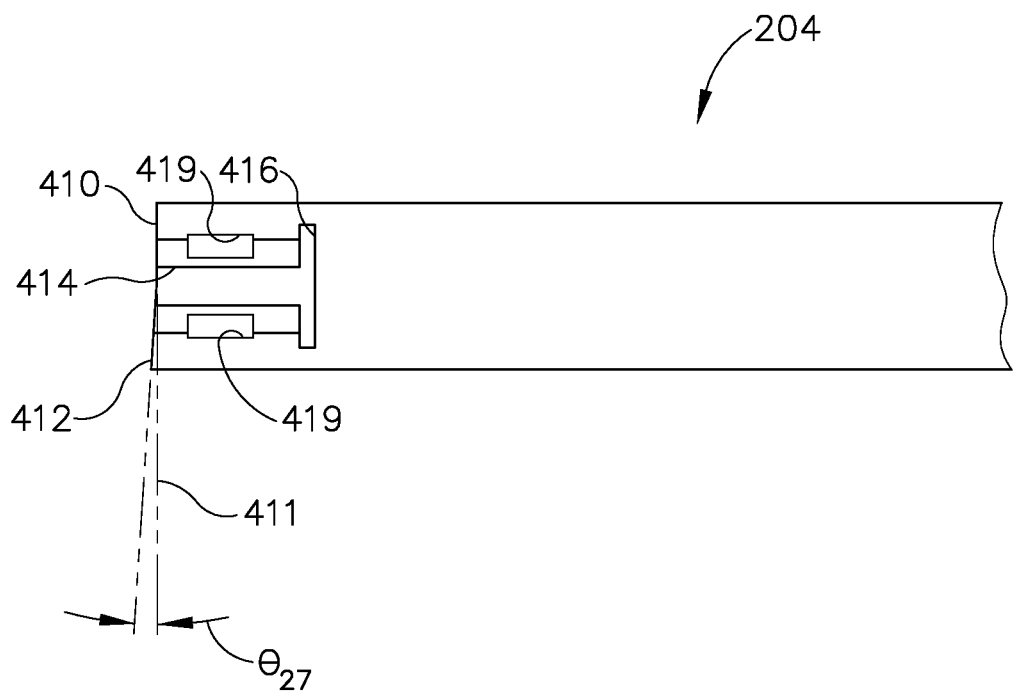
FIG. 27 depicts a top elevational view of the proximal tube member of FIG. 26.

Proximal outer sheath (204) of the present example, referring to FIGS. 14-16 and 26-27, is suitable for incorporation into instrument (10) in a manner substantially similar to outer sheath (32). Proximal outer sheath (204) is substantially similar to outer sheath (32), except for the differences discussed herein. Particularly, proximal outer sheath (204) includes a proximal end (not shown), a distal end (406), and a lumen (408) extending therebetween. As best seen in FIG. 27, a first portion (410) of distal edge extends along an imaginary plane (411) that is perpendicular to the longitudinal axis of proximal outer sheath (204), while a second portion (412) of distal edge (410) extends at an oblique angle ($\theta_{27}$) relative to plane (412). Proximal outer sheath (204) further comprises a longitudinal channel (414) extending from distal edge (410) in a direction parallel to a longitudinal axis of proximal outer sheath (204). Longitudinal channel (414) terminates at a transverse channel (416). Transverse channel (416) of the present example extends parallel to plane (412) but perpendicular relative to longitudinal channel (414). Proximal outer sheath (204) of the present example further comprises a pair of apertures (419), which are generally rectangular in shape, and spaced laterally from one another and from longitudinal cutout (414). Various suitable ways in which proximal outer sheath (204) may be configured will be apparent to those of ordinary skill in the art in view of the teachings herein.

Figure 28:
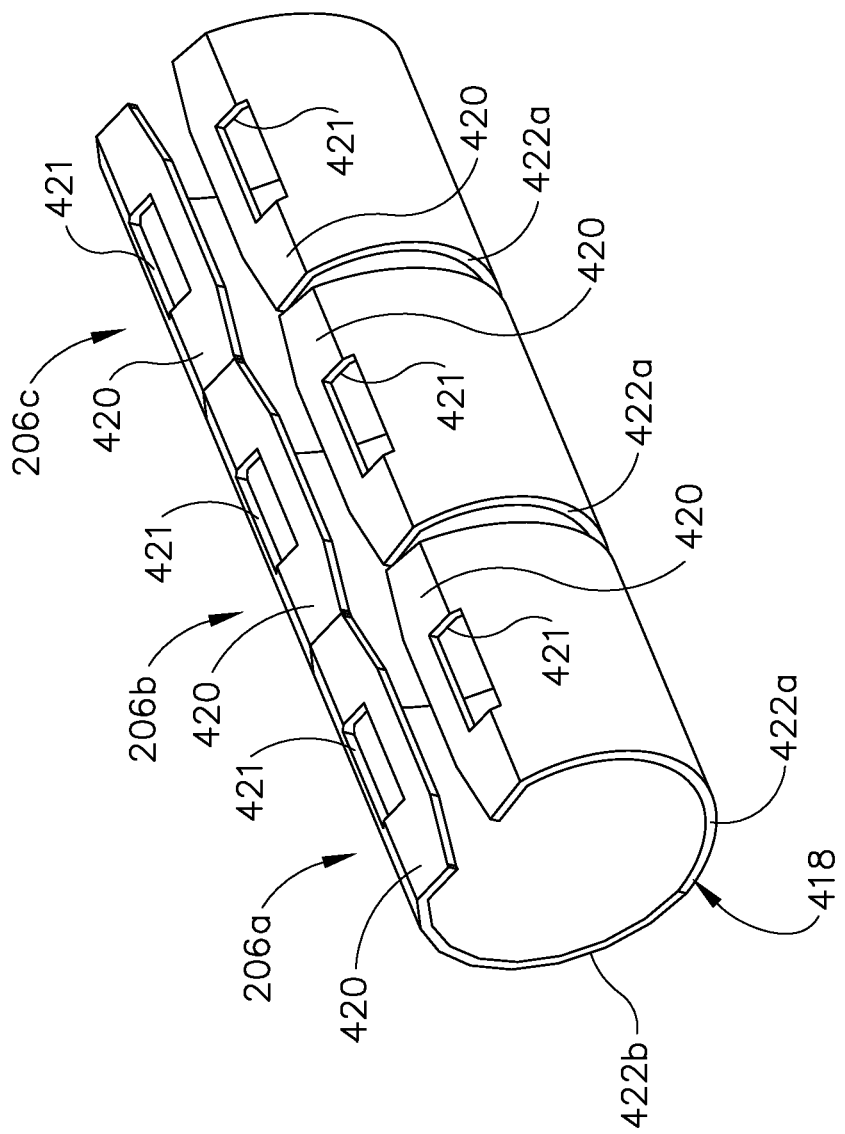
FIG. 28 depicts a perspective view of a plurality of flex rings of the articulation section of FIG. 14 in an unflexed configuration.

As shown in FIGS. 14-16, distal, middle, and proximal flex rings (206a-c) are positioned between distal outer sheath (202) and proximal outer sheath (204) such that flex rings (206a-c), distal outer sheath (202), and proximal outer sheath (204) define at least a portion of a radially outward boundary of shaft assembly (200). Flex rings (206a-c) define a single, unitary body (364) comprising three members (306a-c), with living hinges (366) between adjoining flex rings (206a-c). However, in other examples, flex rings (206a-c) may be separate, individual members. Referring also to FIGS. 28-29B, three flex rings (206a-c) are shown, but it will be understood that there may be more or less than three flex rings (206a-c). In the present example, each flex ring (206a-c) includes a first portion (418) that is partially circular in cross-section and a pair of flanges (420). The flanges (420) of each pair of flanges (420) extend radially inwardly from each end of the first portion (418) toward one another, and along a plane extending parallel to a longitudinal axis of each flex ring (206). Each flange (420) includes a generally rectangular aperture (421) extending therethrough.

Each flex ring (206a-c) includes a first distal edge portion (422a), second distal edge portion (422b), first proximal edge portion (424a), and second proximal edge portion (424b). In the present example, first distal edge portion (422a) extends at an oblique angle relative to second distal edge portion (422b). Second distal edge portion (422b) of each flex ring (206a-c) extends along a first plane (426) that is perpendicular to the longitudinal axis of each flex ring (206a-c). Thus, the first distal edge portion (422a) extends at an oblique angle ($\theta_{29A-1}$) relative to a first plane (426) that is perpendicular to the longitudinal axis of each flex ring (206). Similarly, first proximal edge portion (424a) extends at an oblique angle relative to second proximal edge portion (424b). Second proximal edge portion (424b) extends along a second plane (428) that is perpendicular to the longitudinal axis of each flex ring (206a-c). Thus, the first proximal edge portion (424a) of each flex ring (206a-c) extends at an oblique angle ($\theta_{29A-2}$) relative to its second proximal edge portion (424b).

Figure 29A:
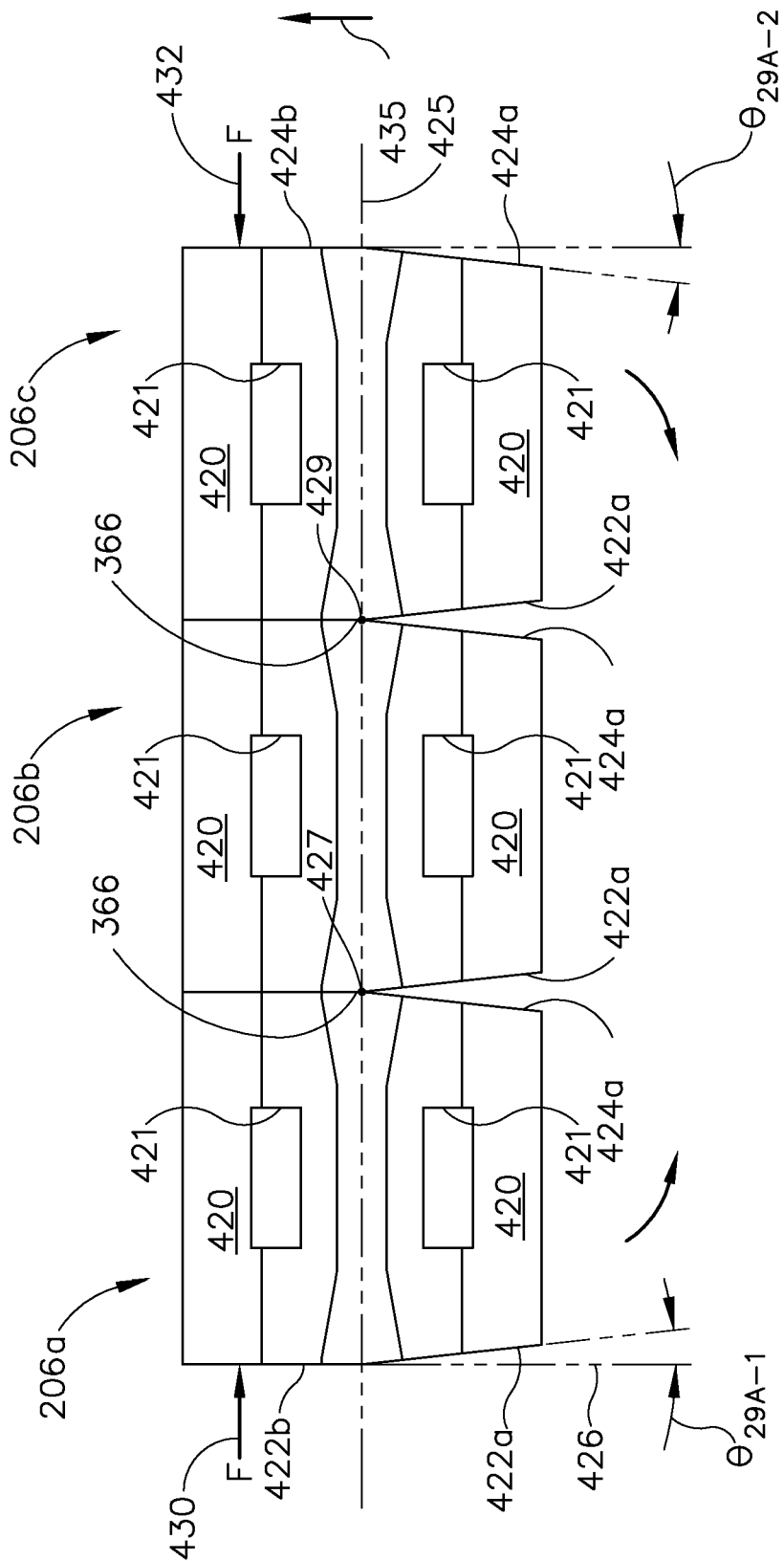
FIG. 29A depicts a top elevational view of the plurality of flex rings of FIG. 28, in an unflexed configuration.
Figure 29B:
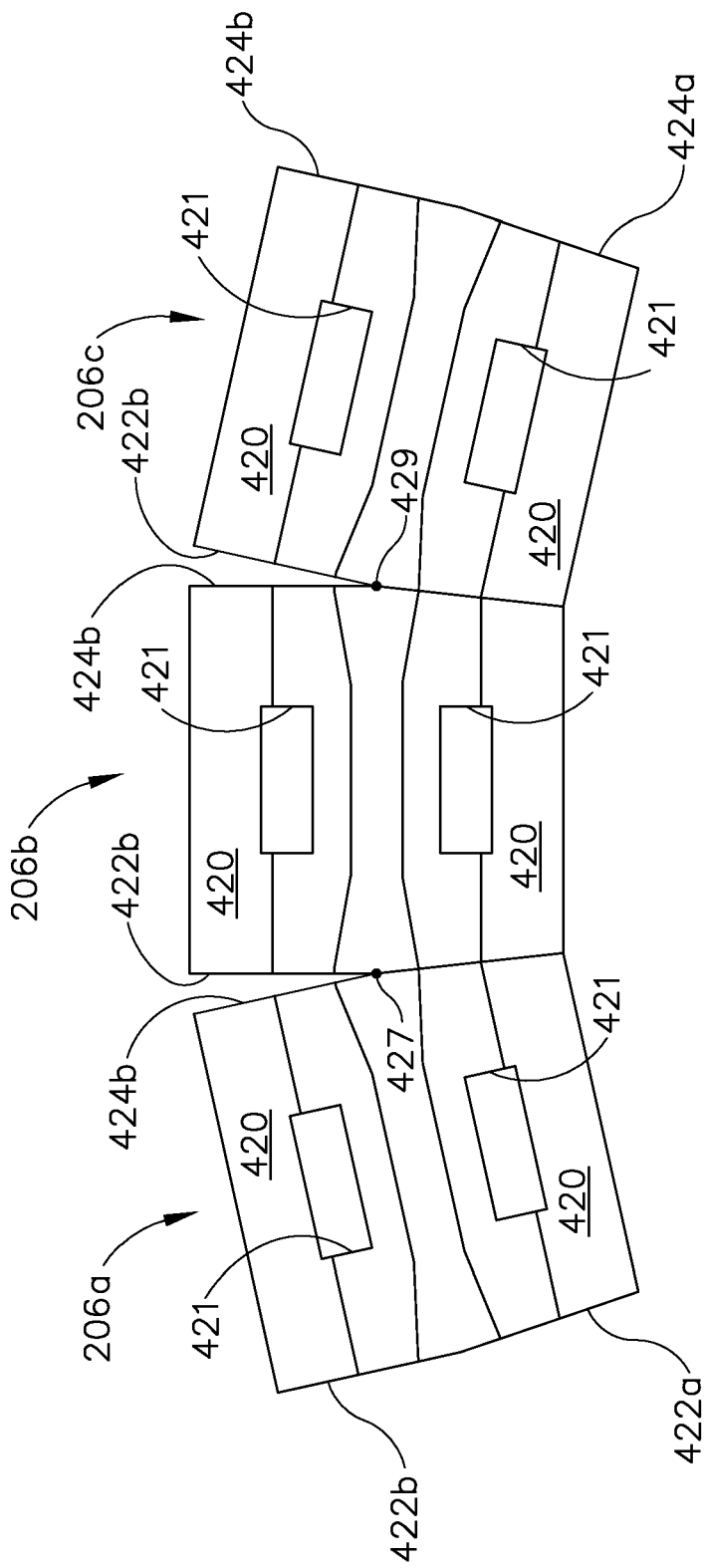
FIG. 29B depicts a top elevational view of the set of flex rings of FIG. 28, in a flexed configuration.

When assembled as shown in FIGS. 14-15, the distal most flex ring (206a) is substantially abutted distally by distal outer sheath (202) (force represented by arrow (430) in FIG. 29A), while the proximal most flex ring (206c) is substantially abutted proximally by proximal outer sheath (204) (force represented by arrow (432) in FIG. 29A). Flex rings (206a-c) are configured to transition to a flexed position (FIG. 29B) from an unflexed position (FIG. 29A) when, for example, articulation bands (212, 214) are moved longitudinally relative to one another, as discussed in more detail below. However, second distal edge portions (424a) and second proximal edge portions (424b) interact with one another and with distal outer sheath (202) and proximal outer sheath (204) to act as positive stops to restrict pivoting of flex rings (206a-c) to a single direction. As shown, longitudinal axis (425) intersects the points of each flex ring (206a-c) where the respective first and second distal portions (422a, 422b) meet, and where the respective first and second proximal portions (424a, 424b) meet. Because adjacent second distal and proximal portions (422b, 424b) act as a positive stop against one another (and also with adjacent distal and proximal tube members (202a, 202b)), flex rings are substantially prevented from pivoting along a path that is above axis (425) ("above" direction represented by arrow (435)). Therefore, in the present example, due to the operative coupling of flex rings (206a-c) to other components of articulation mechanism (210), articulation mechanism (210) is permitted to articulate in only one direction (opposite to arrow (435)) and may only pivot about axes (427, 429)).

Flex rings (206a-c) are rigid in the present example such that any attempted articulation in the opposite direction does not substantially occur due to the material properties of flex rings (206a-c). That is, where articulation bands (212, 214) are moved in a manner that causes a moment in the opposite direction, the material properties (rigidity, stiffness, etc.) of flex rings (206a-c) are configured to prevent bending, buckling, compression, etc., of the flex rings (206a-c) that may cause a certain amount of articulation in the direction of arrow (435). Various suitable ways in which flex rings (206a-c) may be configured will be apparent to those of ordinary skill in the art in view of the teachings herein.

FIGS. 14-16 and 30-33B show collar (300) of the present example. As noted above, collar (300) is configured to operably couple certain components of the articulation section (210) to one another. Collar (300) of the present example is further configured to couple distal outer sheath (202) with proximal outer sheath (204). As best shown in FIGS. 30-31, collar (434) includes a proximal end (436), and a distal end (438), and a body (440) extending therebetween. In the present example, collar (300) includes a spine portion (442) extending along a longitudinal axis and five pairs of opposing legs (444a-e) extending from the spine portion (442). Collar (300) also includes an elongate rib (443) extending along the axis of the collar (300). Each of the five pairs of legs (444a-e) are spaced apart equally along a longitudinal axis of the collar (300). As shown, there are five pairs of opposing legs, but there may be more or less than five pairs of legs, and the pairs of opposing legs may or may not be equally spaced longitudinally. In the present example, each pair of legs includes a first leg that extends away from the spine (442) in a first direction and a second leg extending away from the spine in second direction. Each of the first and second legs of each pair include curvilinear portions and are configured such that the first and second legs of each pair eventually extend parallel to one another. Each of the legs (444a-e) includes a respective snap-fit feature (446a-e) defining respective angled portions (448a-e) and lip portions (450a-e). In some examples, angled portions (448a-e) are configured to act as cam members, in order to assist the collar (300) to be coupled with other components of the articulation section. More particularly, angled portions (448a-e) may act as cam members when being directed into respective slots and apertures, and legs (444a-e) may flex inwardly temporarily as collar (300) is being directed into engagement with certain components to provide a snap fit engagement. Various suitable ways in which collar (300) may be configured will be apparent to those of ordinary skill in the art in view of the teachings herein The operable coupling of components of the articulation section (210) allows the articulation section (210) to articulate when a moment is applied directly to one or more components of the articulation section (210). Referring to FIGS. 14-16, 32A and 33A, in the present example, in the unarticulated configuration, proximal end (314) of distal flex member (302) substantially abuts flex base member (306a), particularly at the point where first distal portion (382a) meets second distal portion (382b). Distal end (340) of proximal flex member (304) substantially abuts flex base member (306c), particularly where first proximal portion (384a) meets second proximal portion (384b). As discussed above, flex base member (306b) is between flex base member (306a) and flex base member (306c).

In the present example, lumen (390) of distal tube member (302) coaxially receives distal flex member (302) such that slots (334) of distal flex member (302) generally align with apertures (400) of distal outer sheath (202). Legs (444a) extend into apertures (400) and along slots (334) such that lip portion (450a) engages a portion of aperture (336) and thereby secures collar (300), distal flex member (302), and distal outer sheath (202) to one another. Lumen (408) of proximal outer sheath (204) receives proximal flex member (304) such that slots (360) of proximal flex member (304) generally align with apertures (419) of proximal tube member. Legs (444e) extend into apertures (419) and along slots (360) such that lip portion (450e) engages a portion of aperture (362) and thereby secures collar (300), proximal flex member (304), and proximal outer sheath (204) to one another.

Flex base members (306a-c) of the present example are coaxially received in flex rings (206a-c) such that flex base member (306a) is coincident with flex ring (206a), flex base member (306b) is coincident with flex ring (206b), and flex base member (306c) is coincident with flex ring (206c). Therefore, in such a configuration, apertures (421) of each flex ring (206a-c) generally align with slots (378) of a respective flex base member (306a-c). Legs (444b) extend into apertures (421) of flex ring (206a) and along slots (378) of flex base member (306a) such that lip portions (450b) engage a portion of a respective aperture (380). Similarly, legs (444c) extend into apertures (421) of flex ring (206b) and along slots (378) of flex base member (306b) such that lip portions (450c) engage a portion of a respective aperture (380). Similarly, legs (444d) extend into apertures of flex ring (206b) and along slots (378) of flex base member (306c) such that lip portions (450d) engage a portion of a respective aperture (380).

Still referring to FIGS. 14-16, 32A, and 33A, in the present example, in the unarticulated configuration, first portion (392) of proximal edge of distal outer sheath (202) substantially abuts second distal portion (422b) of flex ring (206a). Second proximal portion (424b) of flex ring (206a) substantially abuts second distal portion (422b) of flex ring (206b). Similarly, second proximal portion (424b) of flex ring (206b) substantially abuts second distal portion (422b) of flex ring (206c). Second proximal portion (424b) of flex ring (206b) substantially abuts first portion (210) of distal edge of proximal outer sheath (204). Various suitable ways in which articulation section (210) may be configured will be apparent to those of ordinary skill in the art in view of the teachings herein.

In the present example, as articulation bands (212, 214) are moved longitudinally relative to one another, a moment is initially applied to distal flex member (302). Due to the distal flex member (302), flex base members (306a-c), proximal flex member (304), distal outer sheath (202), flex rings (206a-c), and proximal outer sheath (304) being operably coupled via collar (300) in the manner described herein, the moment applied to distal flex member (302) is transferred to the collar (300), distal flex member (302), flex base members (306a-c), proximal flex member (304), distal outer sheath (202), flex rings (206a-c), and proximal outer sheath (204). Thus, articulation section transitions (210) to an articulated configuration, as best shown in FIGS. 32B, 33B. In the articulated configuration, articulation section (210) articulates in the same direction away from the longitudinal axis of instrument (10) as the direction of the bend angle (A) of blade (260).

As shown in FIGS. 32B and 33B, as a result of the moment applied onto the components of articulation section (210), distal outer sheath (202) is pivoted relative to flex ring (206a) such that second portion (394) of distal edge of distal outer sheath (202) substantially abuts first distal portion (422a) of flex ring (206a). Flex ring (206a) is shown to be pivoted relative to flex ring (206b) such that first proximal portion (424a) of flex ring (206b) substantially abuts first distal portion (422a) of flex ring (206b). Flex ring (206b) is shown pivoted relative to flex ring (206c) such that first proximal portion (424a) of flex ring (206b) substantially abuts first distal portion (422a) of flex ring (206c). Flex ring (206c) is shown to be pivoted such that first proximal portion (424a) of flex ring (206c) substantially abuts second portion (412) of distal edge of proximal outer sheath (204). Thus, in the present example, the maximum articulation angle (as measured between a central axis of distal outer sheath (202) relative to a central axis of proximal outer sheath (204)) due to the abutment of such structures is $\theta_A$, where $\theta_A = 3*(\theta_{29A-1} + \theta_{29A-2}) - \theta_{27} - \theta_{25}$.

Figure 32A:
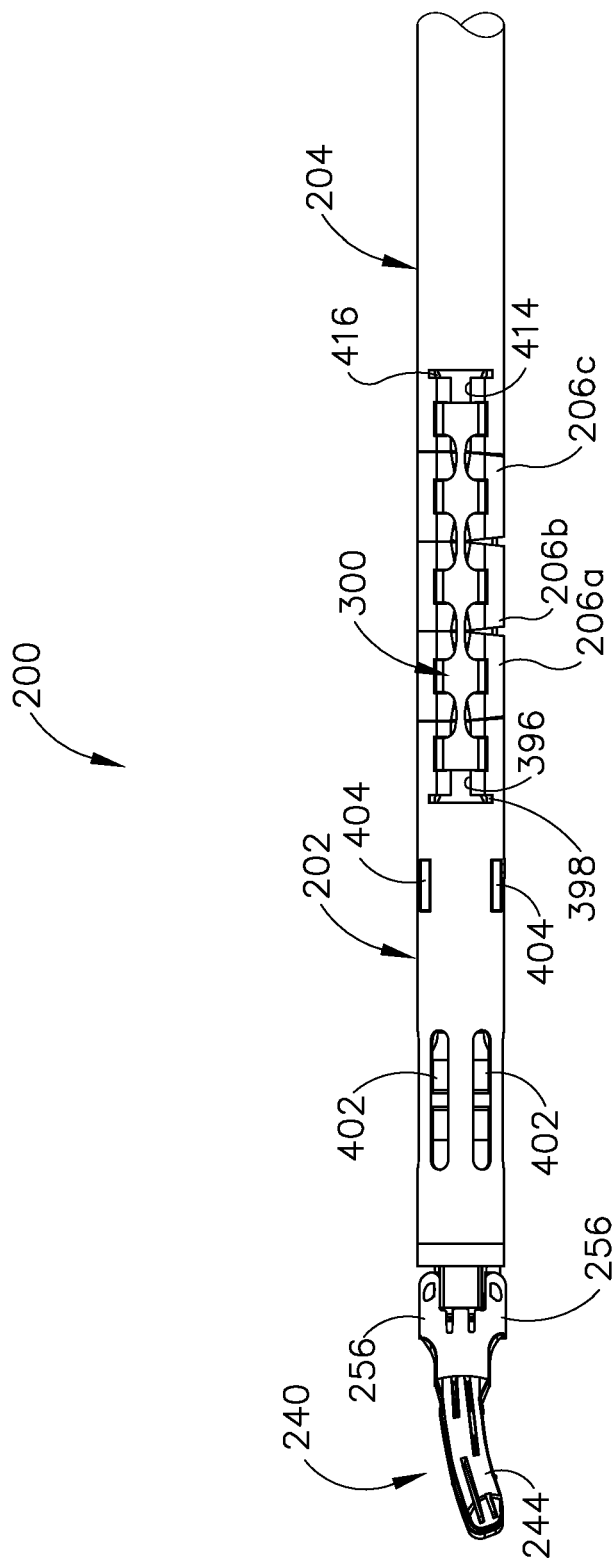
FIG. 32A depicts a top elevational view of the articulation section of the shaft assembly and the end effector of FIG. 14, showing the articulation section in an unarticulated configuration.
Figure 32B:
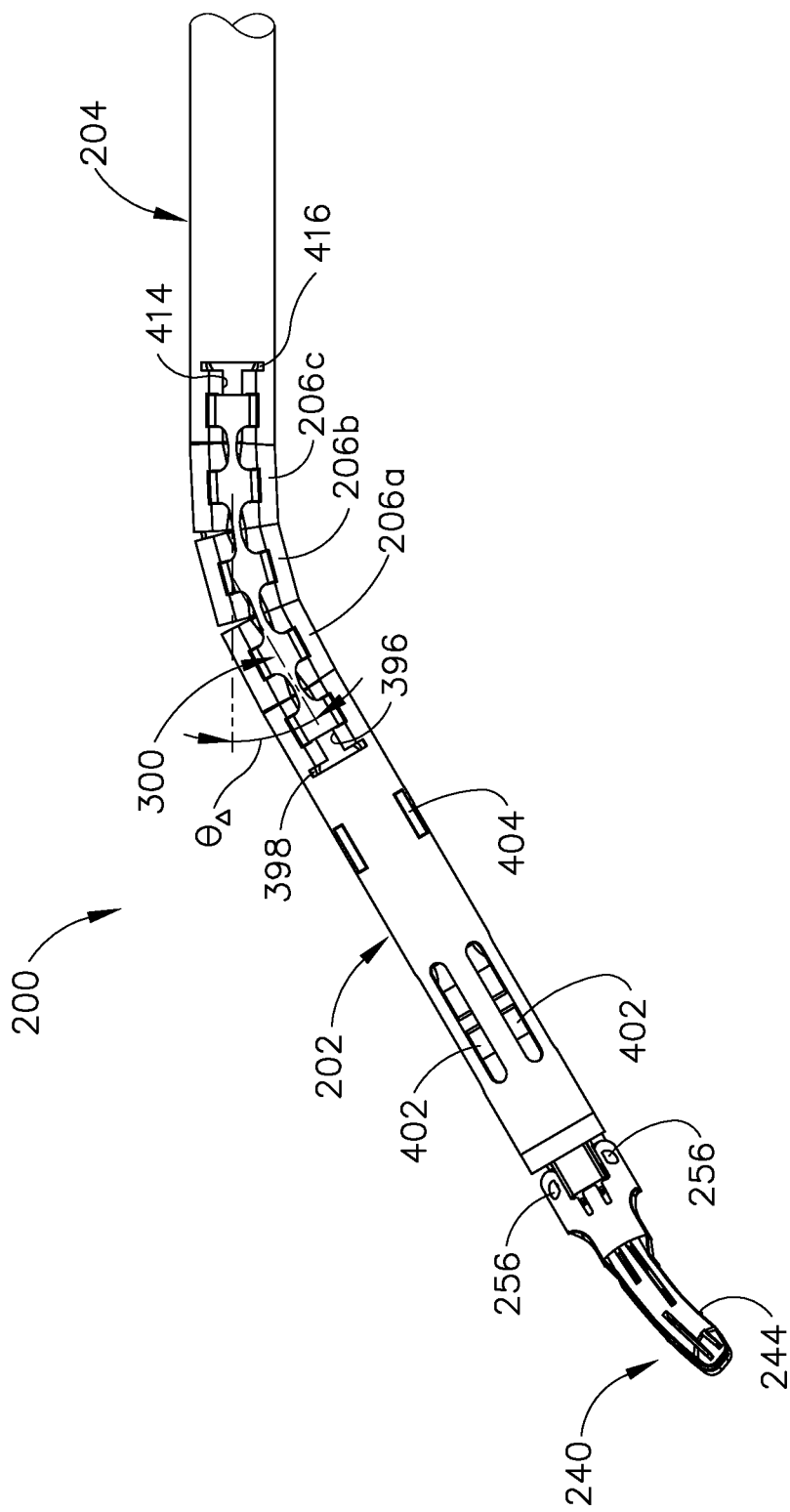
FIG. 32B depicts a top elevational view of the articulation section of the shaft assembly and the end effector of FIG. 14, showing the articulation section in an articulated configuration.
Figure 33A:
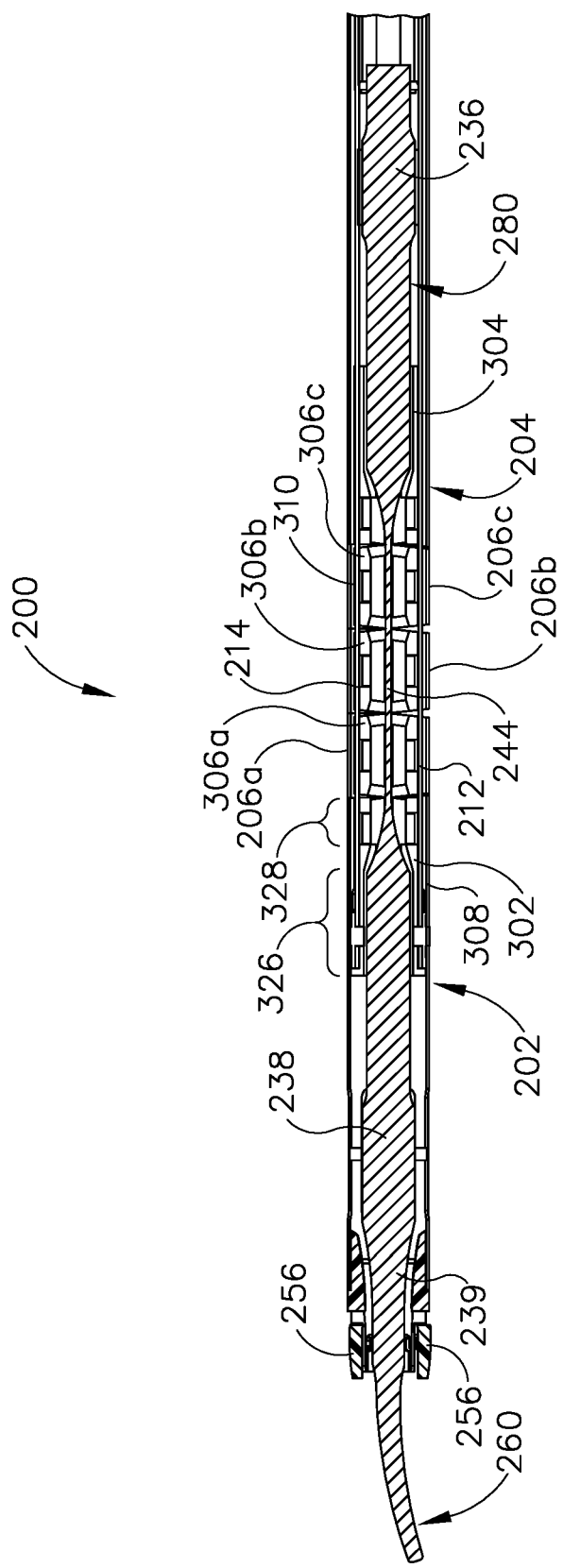
FIG. 33A depicts a top cross-sectional view of the articulation section of the shaft assembly and the end effector of FIG. 14, showing the articulation section in an unarticulated configuration.
Figure 33B:
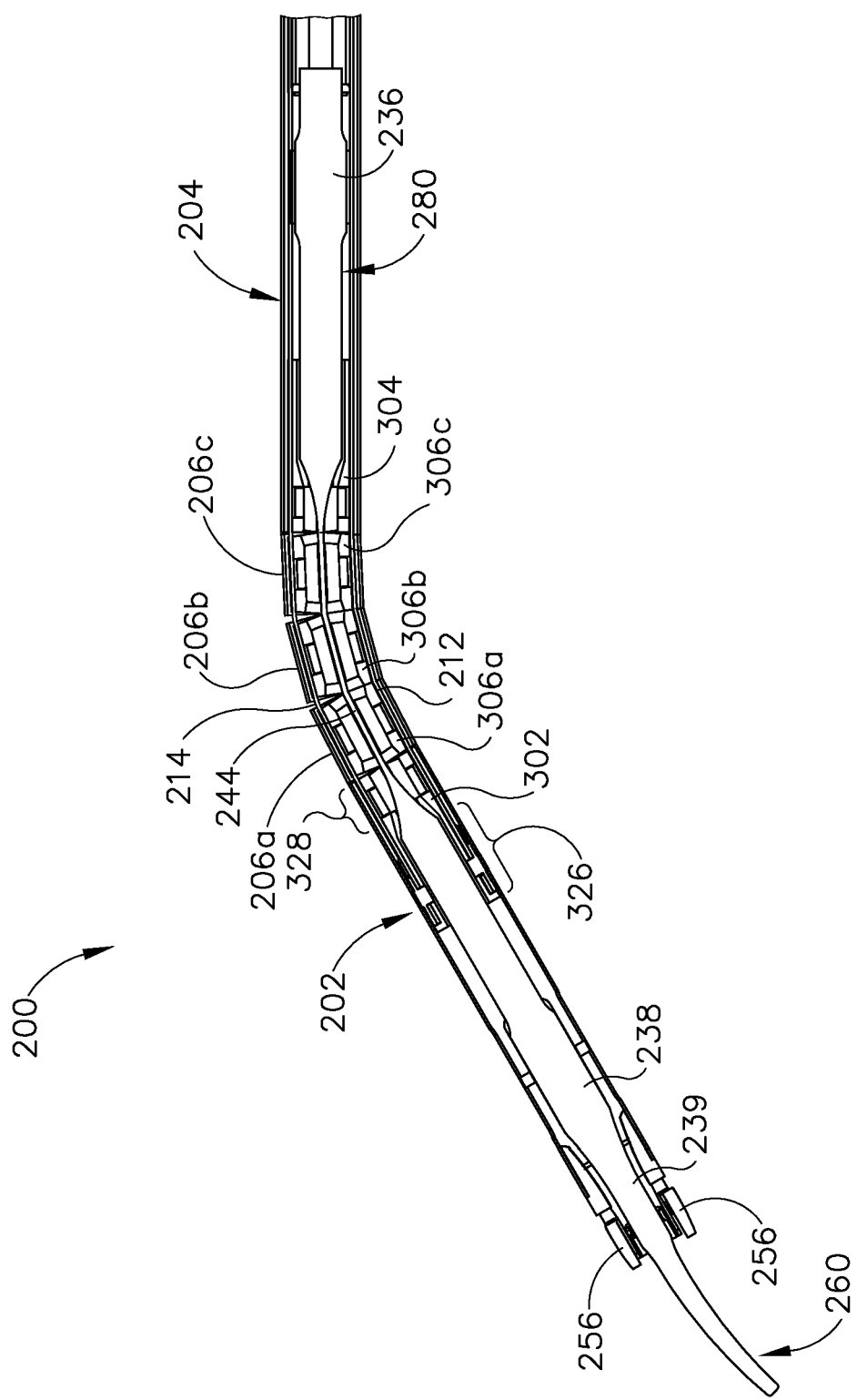
FIG. 33B depicts a top cross-sectional view of the articulation section of the shaft assembly and the end effector of FIG. 14, showing the articulation section in an articulated configuration.

Once the articulation bands (212, 214) move relative to one another in a manner opposite to that which caused the articulation, articulation section (210) may return to the unarticulated configuration shown in FIGS. 32A and 33A. However, even if the operator somehow attempts to continue opposingly move articulation bands (212, 214) once articulation section (210) reaches the unarticulated configuration shown in FIGS. 32A and 33A, engagement between adjacent edge portions (422b, 424b) will prevent articulation section (210) from articulating past longitudinal axis (425) in the direction of arrow (435).

II. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for operating on tissue, the apparatus comprising: (a) a body assembly; (b) a shaft extending distally from the body assembly, wherein the shaft defines a longitudinal axis; (c) an acoustic waveguide, wherein the waveguide comprises a flexible portion; (d) an articulation section coupled with the shaft, wherein a portion of the articulation section encompasses the flexible portion of the waveguide, wherein the articulation section further comprises: (i) a first member, and (ii) a second member, wherein the second member is longitudinally translatable relative to the first member; (e) an end effector comprising an ultrasonic blade in acoustic communication with the waveguide, wherein a distal portion the ultrasonic blade is disposed in a first direction away from the longitudinal axis at a bend angle; and (f) an articulation drive assembly operable to drive articulation of the articulation section to thereby deflect the end effector from the longitudinal axis in the first direction.

Example 2

The apparatus of Example 1 or any of the following examples, wherein the articulation section includes a positive stop, wherein the positive stop is configured to substantially prevent deflection of the end effector in a second direction, wherein the second direction is opposite to the first direction.

Example 3

The apparatus of Example 2, wherein the articulation section comprises a plurality of tubular members, wherein the positive stop is disposed on at least one of the tubular members.

Example 4

The apparatus Example 3, wherein the positive stop comprises an edge of at least one of the tubular members.

Example 5

The apparatus of Example 4, wherein the edge extends perpendicular relative to the longitudinal axis of the shaft when the articulation section is in an unarticulated configuration.

Example 6

The apparatus of any of the preceding or following Examples, wherein the articulation section comprises a flexible collar having a spine portion extending parallel to the longitudinal axis of the shaft, wherein the collar is configured to operably couple the shaft and the articulation section.

Example 7

The apparatus of Example 6, wherein the collar comprises a plurality of legs extending transverse to the spine portion, wherein at least one of the legs is configured to engage the shaft, wherein at least one pair of legs is configured to engage the articulation section.

Example 8

The apparatus of any of the preceding or following Examples, wherein the blade extends in a first direction along a curved path.

Example 9

The apparatus of any of the preceding or following Examples, wherein the articulation section comprises a radially inner portion, wherein the articulation section further comprises a radially outer portion surrounding at least part of the radially inner portion, wherein the radially outer portion is configured to limit articulation of the articulation section to the first direction.

Example 10

The apparatus of Example 9, wherein the radially outer portion comprises a plurality of adjacent, at least partially tubular members.

Example 11

The apparatus of Example 10, wherein at least one of the at least partially tubular members comprises a distal edge, wherein the distal edge includes a first portion that extends at an oblique angle relative to a first plane extending perpendicular relative to the longitudinal axis, wherein the distal edge includes a second portion that extends along the first plane.

Example 12

The apparatus of Example 11, wherein at least one of the at least partially tubular members comprises a proximal edge, wherein the proximal edge includes a first portion that extends at an oblique angle relative to a second plane extending perpendicular to the longitudinal axis, wherein the proximal edge includes a second portion that extends along the second plane.

Example 13

The apparatus of any of Example 12, wherein the second portion of the proximal edge of one of the at least partially tubular members substantially abuts the second portion of the distal edge of an adjacent one of the at least partially tubular members when the articulation section is in an unarticulated configuration.

Example 14

The apparatus of Example 12, wherein the first portion of the proximal edge of one of the at least partially tubular members substantially abuts the first portion of the distal edge of an adjacent one of the at least partially tubular members when the articulation section is in an articulated configuration.

Example 15

The apparatus of Example 9, wherein the radially inner portion defines opposing channels for the first member and the second member, respectively, wherein the first member and the second member are each disposed between the radially inner portion and the radially outer portion.

Example 16

An apparatus for operating on tissue, the apparatus comprising: (a) a body assembly; (b) a shaft extending distally from the body assembly, wherein the shaft defines a longitudinal axis; (c) an acoustic waveguide, wherein the waveguide comprises a flexible portion; (d) an articulation section coupled with the shaft; (e) an end effector coupled with the articulation section, wherein the end effector comprises an ultrasonic blade in acoustic communication with the waveguide; (f) an articulation drive assembly operable to drive articulation of the articulation section to thereby deflect the end effector from the longitudinal axis, wherein the articulation drive assembly comprises: (i) a first member, and (ii) a second member; wherein the first and second members are operable to translate simultaneously in opposite directions to thereby deflect the end effector from the longitudinal axis, wherein the articulation section comprises a stop member configured to substantially prevent the deflection of the end effector from the longitudinal axis in a first direction but allow the deflection of the end effector in a second direction from the longitudinal axis, wherein the second direction is opposite to the first direction.

Example 17

The apparatus of Example 16 or any of the following examples, wherein the stop member is configured to engage at least a portion of the shaft to prevent deflection of the end effector in the second direction.

Example 18

The apparatus of Example 16 or any of the following examples, wherein the stop member is disposed perpendicularly relative to the longitudinal axis.

Example 19

The apparatus of Example 16 or any of the following examples, wherein the end effector further comprises a clamp arm operable to pivot toward and away from the blade.

Example 20

An apparatus for operating on tissue, the apparatus comprising: (a) a body assembly; (b) a shaft extending distally from the body assembly, wherein the shaft defines a longitudinal axis; (c) an articulation section coupled with the shaft; (d) an end effector coupled with the articulation section, wherein the end effector comprises: (i) a working element configured to engage tissue, wherein the working element includes an elongate shaft extending through the shaft of the instrument, and (ii) a clamp arm operable to pivot toward and away from the working element; and (e) an articulation drive assembly operable to drive articulation of the articulation section to thereby deflect the end effector from the longitudinal axis, wherein the articulation drive assembly comprises: (i) a first member, and (ii) a second member; wherein the first and second members are operable to translate simultaneously in opposite directions to thereby deflect the end effector from the longitudinal axis, wherein the articulation section comprises a plurality of pivotable members surrounding the elongate shaft of the working element; wherein the pivotable members are include a stop on one side to resist pivoting in a first direction to thereby prevent articulation of the articulation section; wherein the pivotable members are configured to pivot in a second direction that is opposite to the first direction in response to translation of the first and second members to thereby cause articulation of the articulation section.

III. MISCELLANEOUS

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) an end effector including an ultrasonic blade longitudinally extending from a proximal blade portion toward a distal blade portion and configured to cut a tissue from the proximal blade portion to the distal blade portion; and
   (b) a shaft assembly proximally extending from the end effector, the shaft assembly including:
      (i) a proximal shaft defining a longitudinal axis,
      (ii) a distal shaft having the end effector distally projecting therefrom,
      (iii) an acoustic waveguide in communication with the ultrasonic blade and including a single, unitarily formed flexible portion, and
      (iv) an articulation section projecting between the proximal shaft and the distal shaft and configured to articulate from a straight configuration to an articulated configuration thereby deflecting the end effector a first direction away from the longitudinal axis,
      wherein the articulation section receives the flexible portion of the acoustic waveguide and defines a space radially therebetween surrounding the flexible portion of the acoustic waveguide such that the articulation section does not contact the acoustic waveguide upon articulation from the straight configuration to the articulated configuration,
      wherein the articulation section includes a flexible collar extending from the proximal shaft to the distal shaft and coupled to each of the proximal shaft and the distal shaft to couple the proximal shaft with the distal shaft.

2. The surgical instrument of claim 1, wherein the acoustic waveguide further includes:
   (A) a distal section in communication with the ultrasonic blade,
   (B) a proximal section received within the proximal shaft, and
   (C) the flexible portion extending between the distal and proximal sections, wherein the flexible portion includes a narrowed section structure narrower than the distal and proximal sections of the acoustic waveguide.

3. The surgical instrument of claim 2, wherein the narrowed section structure defines a plane and is configured to flex in a lateral direction perpendicular to the plane upon articulation from the straight configuration to the articulated configuration.

4. The surgical instrument of claim 1, wherein the articulation section further includes:
   (A) a first drive member radially offset from the acoustic waveguide, and
   (B) a second drive member radially offset from the acoustic waveguide and longitudinally translatable relative to the first drive member from a first position to a second position,
   wherein the articulation section is in the straight configuration with the second drive member in the first position and radially offset from the acoustic waveguide, and
   wherein the articulation section is in the articulated configuration with the second drive member in the second position and radially offset from the acoustic waveguide.

5. The surgical instrument of claim 4, wherein the articulation section further includes a distal flex member rigidly secured to the distal shaft such that the distal flex member is configured to deflect relative to the longitudinal axis with the end effector, wherein the distal flex member at least partially defines the space radially surrounding the flexible portion of the acoustic waveguide such that the distal flex member does not contact acoustic waveguide.

6. The surgical instrument of claim 5, wherein the first drive member is secured to the distal flex member, and wherein the second drive member is secured to the distal flex member.

7. The surgical instrument of claim 6, wherein the first and second drive members are configured to translate simultaneously in opposite directions to thereby deflect the end effector from the longitudinal axis.

8. The surgical instrument of claim 5, wherein the articulation section further includes a first flex member and a second flex member, wherein the first and second flex members are positioned between the proximal shaft and the distal flex member and at least partially further define the space radially surrounding the flexible portion of the acoustic waveguide.

9. The surgical instrument of claim 8, wherein the first and second flex members are each positioned radially inward of the first and second drive members such that first and second flex members are each radially between the acoustic waveguide and the first and second drive members.

10. The surgical instrument of claim 9, wherein the flexible collar is coupled to the first and second flex members.

11. The surgical instrument of claim 5, wherein the distal flex member is rigidly secured to the distal shaft.

12. The surgical instrument of claim 4, wherein the flexible collar in the straight configuration extends along a linear path from the proximal shaft to the distal shaft, and wherein the flexible collar in the articulated configuration extends along a curvilinear path from the proximal shaft to the distal shaft.

13. The surgical instrument of claim 12, wherein the linear path and the curvilinear path are the same distance with the articulation section respectively in the straight and articulated configurations.

14. The surgical instrument of claim 12, wherein the articulation section further includes a first flex member positioned between the proximal shaft and the distal shaft and at least partially further defines the space radially surrounding the flexible portion of the acoustic waveguide, wherein the flexible collar is further coupled to the first flex member thereby supporting the first flex member to radially surround and be radially offset from the flexible portion of the acoustic waveguide.

15. The surgical instrument of claim 1, wherein the articulation section further includes a first flex member positioned between the proximal and distal shafts, and wherein the flexible collar is coupled to the first flex member to couple the first flex member with the proximal and distal shafts.

16. The surgical instrument of claim 15, wherein the flexible collar has a distal leg, a first leg, and a proximal leg, wherein the distal leg extends into the distal shaft, wherein the first leg extends into he first flex member, and wherein the proximal leg extends into the proximal shaft.

17. The surgical instrument of claim 1, wherein the proximal shaft has a proximal sidewall, wherein the distal shaft has a distal sidewall, and wherein the flexible collar extends through each of the distal and proximal sidewalls.

18. The surgical instrument of claim 17, wherein the articulation section further includes a distal flex member and a proximal flex member, wherein the distal flex member is received at least partially within the distal shaft such that the distal sidewall is coupled between the distal flex member and the flexible collar, and wherein the proximal flex member is received at least partially within the proximal shaft such that the proximal sidewall is coupled between the proximal flex member and the flexible collar.

19. A surgical instrument, comprising:
(a) an end effector including an ultrasonic blade longitudinally extending from a proximal blade portion toward a distal blade portion and configured to cut a tissue from the proximal blade portion to the distal blade portion; and
(b) a shaft assembly proximally extending from the end effector, the shaft assembly including:
 (i) a proximal shaft defining a longitudinal axis,
 (ii) an acoustic waveguide in communication with the ultrasonic blade and including a flexible portion, and
 (iii) an articulation section projecting between the proximal shaft and the end effector and configured to articulate from a straight configuration to an articulated configuration thereby deflecting the end effector a first direction away from the longitudinal axis,
wherein the articulation section receives the flexible portion of the acoustic waveguide and defines a space radially therebetween surrounding the flexible portion of the acoustic waveguide such that the flexible portion of the acoustic waveguide is radially spaced from the articulation section upon articulation from the straight configuration to the articulated configuration,
wherein the articulation section includes a proximal flex member coupled to the proximal shaft such that at least a portion of the proximal flex member is received within the proximal shaft, wherein the proximal flex member at least partially defines the space surrounding the flexible portion of the acoustic waveguide, and wherein the proximal shaft has a distal edge extending at an oblique angle relative to a plane perpendicular to the longitudinal axis.

20. A surgical instrument, comprising:
(a) an end effector including an ultrasonic blade longitudinally extending from a proximal blade portion toward a distal blade portion and configured to cut a tissue from the proximal blade portion to the distal blade portion; and
(b) a shaft assembly proximally extending from the end effector, the shaft assembly including:
 (i) a proximal shaft defining a longitudinal axis,
 (ii) an acoustic waveguide in communication with the ultrasonic blade and including:
  (A) a distal section in communication with the ultrasonic blade,
  (B) a proximal section received within the proximal shaft, and
  (C) a flexible portion extending between the distal and proximal sections, wherein the flexible portion is a single, unitarily formed narrowed section structure narrower than the distal and proximal sections of the acoustic waveguide and defining a plane, and
 (iii) an articulation section projecting between the proximal shaft and the end effector and configured to articulate from a straight configuration to an articulated configuration thereby flexing the flexible portion in a lateral direction perpendicular to the plane and further deflecting the end effector a first direction away from the longitudinal axis,
wherein the articulation section receives the flexible portion of the acoustic waveguide and defines a space radially therebetween surrounding the flexible portion of the acoustic waveguide such that the flexible portion of the acoustic waveguide between the proximal and distal sections of the acoustic waveguide is radially spaced from the articulation section upon articulation from the straight configuration to the articulated configuration, wherein the articulation section includes a first flex member at least partially defining the space, and wherein the first flex member has a generally U-shaped body.

\* \* \* \* \*